(12) United States Patent
Dempsey et al.

(10) Patent No.: US 8,164,439 B2
(45) Date of Patent: Apr. 24, 2012

(54) ULTRASONIC COMPLIANCE ZONE SYSTEM

(75) Inventors: Michael K. Dempsey, Groton, MA (US); Ronald S. Newbower, Acton, MA (US)

(73) Assignee: The General Hospital Corp., Boston, MA (US)

( * ) Notice: Subject to any disclaimer, the term of this patent is extended or adjusted under 35 U.S.C. 154(b) by 552 days.

(21) Appl. No.: 12/487,366

(22) Filed: Jun. 18, 2009

(65) Prior Publication Data
US 2010/0321180 A1   Dec. 23, 2010

(51) Int. Cl.
G08B 1/08 (2006.01)
G08B 23/00 (2006.01)
H04B 1/02 (2006.01)

(52) U.S. Cl. ............. 340/539.12; 340/572.1; 340/573.1; 340/566; 340/943; 367/137; 367/197; 700/111

(58) Field of Classification Search ............... 340/539.12
See application file for complete search history.

(56) References Cited

U.S. PATENT DOCUMENTS

| | | |
|---|---|---|
| 5,202,666 A | 4/1993 | Knippscheer |
| 5,610,589 A | 3/1997 | Evans et al. |
| 5,812,059 A | 9/1998 | Shaw et al. |
| 5,952,924 A | 9/1999 | Evans et al. |
| 6,236,317 B1 | 5/2001 | Cohen et al. |
| 6,392,546 B1 | 5/2002 | Smith |
| 6,426,701 B1 | 7/2002 | Levy et al. |
| 6,574,482 B1 | 6/2003 | Radomsky et al. |
| 6,727,818 B1 | 4/2004 | Wildman et al. |
| 6,882,278 B2 | 4/2005 | Winings et al. |
| 6,883,563 B2 | 4/2005 | Smith |
| 6,956,498 B1 | 10/2005 | Gauthier et al. |
| 6,975,231 B2 | 12/2005 | Lane et al. |
| 6,977,579 B2 | 12/2005 | Gilfix et al. |
| 7,015,816 B2 | 3/2006 | Wildman et al. |
| 7,099,649 B2 | 8/2006 | Patterson et al. |
| 7,099,895 B2 | 8/2006 | Dempsey |
| 7,242,307 B1 | 7/2007 | LeBlond et al. |
| 7,348,736 B2 | 3/2008 | Piepgras et al. |
| 7,403,111 B2 | 7/2008 | Tessier et al. |
| 7,480,567 B2 | 1/2009 | Suomela et al. |
| 7,496,445 B2 | 2/2009 | Mohsini et al. |

(Continued)

OTHER PUBLICATIONS

Infection Prevention Systems, How clean are your employees', www.cleanerhands.net.

(Continued)

*Primary Examiner* — Donnie Crosland
(74) *Attorney, Agent, or Firm* — Nutter McClennen & Fish LLP

(57) ABSTRACT

A system is provided for establishing a compliance zone and monitoring interactions therewith. The system includes a compliance zone designator and a wearable device. The compliance zone designator transmits an ultrasound signal to establish the compliance zone. The ultrasound signal may be encoded with information on the compliance zone. The compliance zone designator is configured for placement at a location in which the compliance zone is desired. The wearable device is separate from the compliance zone designator. The wearable device includes a compliance zone recognition component configured to recognize the compliance zone and identify one or more pre-defined interaction criteria for the compliance zone. When the wearable device is within the compliance zone, the compliance zone recognition component recognizes the compliance zone and identifies the interaction criteria of the compliance zone. Based on the interaction criteria the wearable device determines and records compliance with the interaction criteria. The recorded data is optionally used to set off real-time alerts. The recorded data is also optionally used in subsequent analysis and documentation of compliance with protocols.

34 Claims, 19 Drawing Sheets

U.S. PATENT DOCUMENTS

| | | |
|---|---|---|
| 7,577,444 B2 | 8/2009 | Bird et al. |
| 7,620,493 B2 | 11/2009 | Stankiewicz et al. |
| 7,770,782 B2 | 8/2010 | Sahud |
| 7,818,083 B2 | 10/2010 | Glenn et al. |
| 2004/0150527 A1 | 8/2004 | Harper et al. |
| 2005/0248461 A1 | 11/2005 | Lane et al. |
| 2007/0008146 A1 | 1/2007 | Taylor et al. |
| 2007/0020212 A1 | 1/2007 | Bernal et al. |
| 2007/0257803 A1 | 11/2007 | Munro et al. |
| 2008/0100441 A1 | 5/2008 | Prodanovich et al. |
| 2008/0120029 A1 | 5/2008 | Zelek et al. |
| 2008/0246599 A1 | 10/2008 | Hufton et al. |
| 2009/0184823 A1 | 7/2009 | Tessier |
| 2009/0189759 A1 | 7/2009 | Wildman et al. |

OTHER PUBLICATIONS

International Search Report and Written Opinion, from PCT/US10/039002, mailed Feb. 9, 2011.

International Search Report and Written Opinion for Application No. PCT/US2011/029549, mailed Feb. 9, 2011.

InterActive Wayfinding Software, http://www/here2theresoftware.com.

ULTRASONIC COMPLIANCE ZONE SYSTEM

FIELD OF THE INVENTION

Exemplary embodiments of the present invention relate to monitoring and enforcing protocols in facilities. More specifically, exemplary embodiments relate to establishing designated compliance zones through transmission of data using ultrasound signals, and monitoring interactions with the designated compliance zones to determine compliance with protocols.

BACKGROUND OF THE INVENTION

Many facilities have protocols in place to comply with health, safety, insurance, and regulatory requirements. In large facilities, such as factories and hospitals, there may be a large number of people, equipment, areas, and other resources that need to be tracked in the enforcement of protocols. In addition to the large numbers involved, there may also be many different types of people, equipment, areas, and resources in such large facilities. Each of the different types of people, equipment, areas, and resources may have different types of associated protocols.

As an example of a compliance protocol, there may be specific areas or zones in a facility that only qualified personnel are allowed to access. In factories, these compliance zones may be hazardous zones where dangerous equipment or chemicals are used, and that only qualified personnel with appropriate safety gear are allowed to access. The level of qualification required for a zone may range from requiring a hard-hat when in the zone to requiring a protective suit and respirator when in the zone. Facilities may also have other zones, such as clean rooms and secure rooms, where certain protocols must be observed. Access to these zones may require personnel to have specific training or security clearance or to take certain actions when entering, exiting or remaining within the zones.

Hospitals also have to regularly monitor and enforce numerous protocols that vary with the different types of people (non-employee and types of employees), equipment, areas, and resources involved. At any given time, in addition to the medical professionals, administrative staff, and housekeeping staff, there are a number of patients, visitors, consultants, contractors, and the like, in the hospital. Each of these individuals may have different protocol requirements associated with them. Hospitals may also have several areas with specific protocol requirements, such as, patient rooms, laboratories, surgical theaters, clean rooms, intensive care areas, quarantined areas, radiology, record rooms, administrative offices, data and security centers, medical supply rooms. Each of these areas may require different protocols. Hospitals may also require the use of temporary or non-permanent protocols. For example, a protection protocol may be required for a specific patient or piece of equipment. A patient or bed holding a patient may be designated as contagious, and only appropriately qualified and equipped medical professionals may be allowed in proximity of the patient or bed. In some circumstances, medical professionals may be required to comply with typical or atypical protocols, such as the use of an N95 respirator when in proximity of patients with certain diagnoses or the need for washing hands when exiting a compliance zone. Other protocols may be generic to a type of person or area.

Enforcement of even simple protocols may be difficult when dealing with a large and busy facility like a hospital, and real time enforcement may be extremely difficult. An exemplary hospital protocol is a hand hygiene or hand washing protocol. Studies indicate that proper adherence to hand hygiene protocols can significantly reduce morbidity and mortality rates caused by hospital-acquired infections. However, enforcement of the behaviors specified in hand hygiene protocols can be difficult in a hospital due to the large number of individuals requiring monitoring and the generally busy fast-paced environment inside a hospital.

Some techniques of monitoring compliance with protocols involve establishing zones within the facility in which each zone has particular protocols associated with it. For example, a clean zone around a patient's bed may require a hand washing protocol to prevent contamination of the clean zone. These techniques monitor interactions of a resource, e.g. hospital staff, with a zone to determine whether the resource has complied with a protocol associated with the zone.

Some conventional techniques of establishing a zone involve transmitting infrared (IR) signals to designate the boundaries of the zone. Infrared signals are line-of-sight (LOS), i.e. the signals propagate in a straight line and generally cannot travel through or around obstacles. Infrared is suitable for some conventional zone-establishing systems because infrared signals do not penetrate walls and can be contained within well-defined zones.

However, there are significant drawbacks to conventional techniques of establishing zones with the transmission of infrared signals. Generally, conventional systems do not work if the line-of-sight between an infrared transmitter and an infrared receiver is blocked, e.g. if a receiver badge worn by a clinician is covered by the clinician's clothing or the protective garb that is required to be worn in certain patient rooms. As such, infrared signal receivers on clinician-worn badges must always be exposed outside the clothing. This often requires uncomfortable or undesirable placement of the badges, e.g. at the back of the neck or shoulder. Exposure of the badges outside the clothing also breaches the infection control barrier of the clothing, which makes the infrared receiver badges unsuitable for use in clean areas. Hospital staff-members wearing infrared receiver badges thus need to be conscious of how and where they wear the badges. For similar reasons, infrared transmitters that indicate use of a hand-washing station cannot be integrated into a hand-washing dispenser because the infrared signals do not penetrate the dispenser casing.

Infrared signals are also susceptible to shadowing, which occurs when an obstacle obscures the main signal path between the infrared transmitter and receiver. Conventional techniques attempt to overcome the problem of shadowing by using a large and complex set of infrared transmitters to establish a single zone. These conventional techniques are expensive to install and require an extensive infrastructure.

Other conventional techniques of establishing a zone involve transmitting radio frequency (RF) signals or Radio Frequency Identification (RFID) signals to designate the boundaries of the zone. Radio frequency signals are not line-of-sight and can generally travel through or around obstacles. This characteristic allows radio frequency receivers, e.g. on clinician-worn badges, to reliably receive signals from a radio frequency transmitter substantially regardless of the topography of the zone. However, this non-line-of-sight characteristic also means that the radio frequency signals can penetrate walls, and cannot reliably be contained within zones that are defined between a set of walls. For example, a radio frequency signal transmitting in a room to define a zone within the room may be received by radio frequency receivers outside the zone in adjacent rooms. Thus, in these conventional systems, a radio frequency receiver may have difficulty in identifying the source of a received signal.

Despite the above shortcomings, both infrared and radio frequency signals have served as preferred technologies for establishing zones over other technologies such as ultrasound. Ultrasound signals are not suitable for data transmission. Ultrasound signals are very prone to multipath interference, which is a phenomenon whereby a wave from a source travels to a detector via two or more paths and, under the right condition, the two or more components of the wave interfere.

SUMMARY

In view of the above, exemplary embodiments provide a system to monitor and encourage compliance with protocols associated with areas and individuals. The system monitors behavior associated with protocols, and determines compliance of the behavior with the protocols. The system is configurable, as necessary, based on the area or individuals involved.

For example, the system provided by exemplary embodiments is capable of establishing compliance zones, and monitoring the behavior of various individuals in and near the compliance zones. A compliance zone may be established using a signal transmission from a compliance zone designator. Each individual interacting with the compliance zone is provided with a wearable device. The wearable device recognizes a signal transmitted by the compliance zone designator, and identifies one or more predetermined or pre-defined criteria for interacting with the compliance zone. These criteria may relate to one or more protocols associated with the compliance zone, and may be configurable as necessary to influence, monitor, and document behavior to enforce a protocol. The system determines whether the wearer of the wearable device complies with the criteria and, therefore, with the protocol associated with the compliance zone.

Furthermore, in view of the drawbacks of using infrared and radio frequency signal transmissions in establishing zones and despite the conventional view that ultrasound is not appropriate for data transmission, the system provided by exemplary embodiments uses ultrasound transmissions to establish zones. Ultrasound is less line-of-sight than infrared and more line-of-sight than radio frequency. Since ultrasound signals are not completely blocked by obstacles, transmitters and receivers can communicate reliably using ultrasound regardless of the topography of the zone. On the other hand, since ultrasound signals cannot penetrate through walls, the system ensures that a zone is well-defined and that the transmission of an ultrasound signal establishing a zone is not received by receivers outside the zone. Although ultrasound signals are not suited to data transmission, exemplary embodiments provide systems and methods for encoding data in ultrasound signals and decoding data from encoded ultrasound signals. Exemplary systems and methods also mitigate the problem of multipath interference associated with ultrasound signals.

In accordance with one exemplary embodiment of the present invention, a system is provided for establishing a compliance zone and monitoring interactions therewith. The system includes a compliance zone designator configured to transmit data using an ultrasound system in such a way that results in the creation of the compliance zone in a vicinity of the compliance zone designator. The ultrasound signal includes a burst of between eight carrier cycles per burst and ten carrier cycles per burst, inclusive. The system also includes a wearable device separate from the compliance zone designator. The wearable device includes a compliance zone recognition component configured to identify a predefined interaction criterion for the compliance zone when the wearable device receives data through the ultrasound signal within the compliance zone. Upon the wearable device being disposed within the compliance zone, the compliance zone recognition component identifies the interaction criterion of the compliance zone and operates in accordance with the interaction criterion. The wearable device also determines and records compliance with the interaction criterion of the compliance zone. The recorded data is optionally used to set off real-time alerts. The recorded data is also optionally used in subsequent analysis and documentation of compliance with protocols.

In accordance with another exemplary embodiment of the present invention, a method is provided for establishing a compliance zone and interacting therewith. The method includes transmitting data using an ultrasound signal using a compliance zone designator in such a way that results in creation of the compliance zone in a vicinity of the compliance zone designator, the ultrasound signal comprising a plurality of bursts, wherein consecutive bursts within the plurality of burst are separated in time by predefined time intervals, and wherein a sequence of all the predefined time intervals between the consecutive bursts within the plurality of bursts uniquely identifies the compliance zone. The method also includes identifying a pre-defined interaction criterion for the compliance zone using a compliance zone recognition component of a wearable device when the wearable device receives the data through the ultrasound signal within the compliance zone, wherein the compliance zone recognition component operates in accordance with the interaction criterion.

In accordance with yet another exemplary embodiment of the present invention, a method is provided. The method includes transmitting a first ultrasound signal in such a way that results in creation of a compliance zone in a vicinity of the transmission of the first ultrasound signal, transmitting a first ultrasound signal in such a way that results in creation of a compliance zone in a vicinity of the transmission of the first ultrasound signal, and identifying an interaction criterion associated with the compliance zone using the first wearable device when the first wearable device receives the first ultrasound signal within the compliance zone. The method also includes performing an action associated with the interaction criterion using the first wearable device, the action including transmitting a second ultrasound signal communicating with a second wearable device. The method further includes receiving the second ultrasound signal from the first wearable device at the second wearable device, and recording receipt of the second ultrasound signal at the second wearable device.

BRIEF DESCRIPTION OF THE FIGURES

These and other characteristics of the present invention will be more fully understood by reference to the following detailed description in conjunction with the attached drawings, in which.

DETAILED DESCRIPTION OF THE INVENTION

Figure 1:
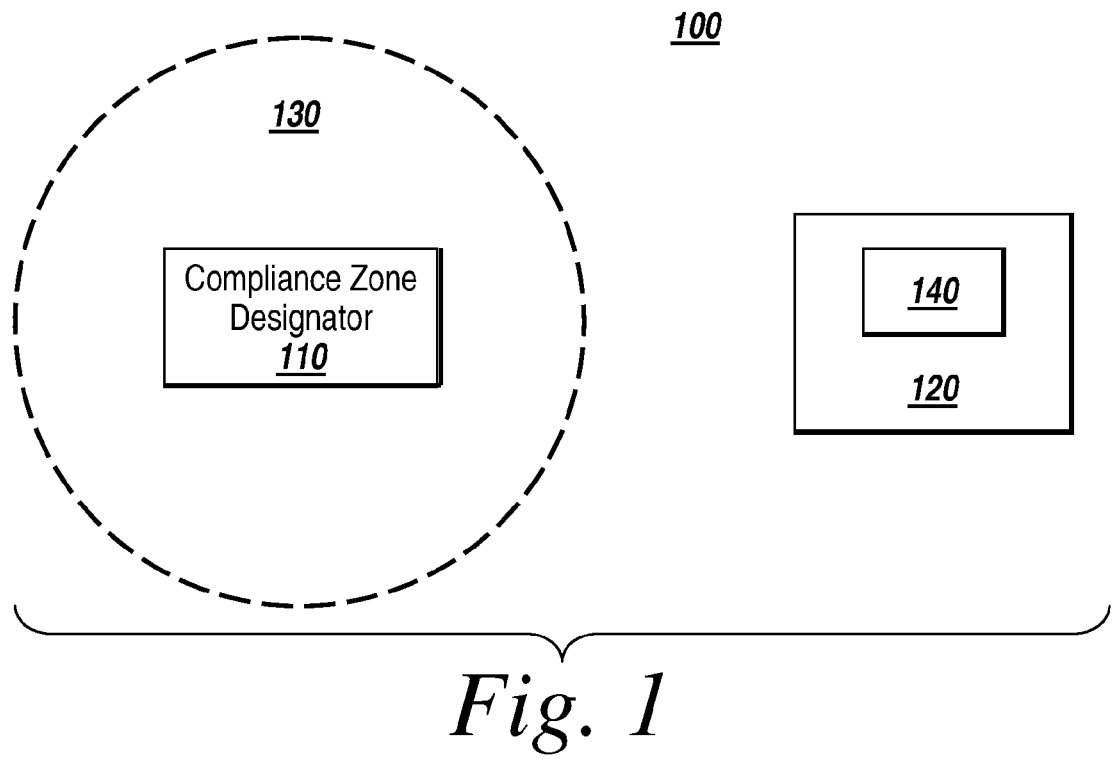
FIG. 1 depicts a block diagram of an exemplary embodiment of a system for establishing a compliance zone and monitoring interaction therewith.

Exemplary embodiments provide systems and methods for enforcing protocols relating to the use of and/or interactions with specified areas in facilities. In order to enforce protocols relating to these specified areas, the system establishes what is referred to herein as a compliance zone in areas where protocol enforcement is desired. In some exemplary embodiments, the compliance zone may be established in a protected area, e.g. around a patient or in a clean area. In these embodiments, the compliance zone may be considered to be a protected zone.

The system establishes these compliance zones using compliance zone designators. The compliance zone designators establish the compliance zone by transmitting one or more ultrasound signals. The area blanketed by the signal is commensurate with the area of the compliance zone. Therefore, the transmission of the signal is the action that establishes the compliance zone.

Individuals interacting with the area of the compliance zone are provided with wearable devices that receive the signals transmitted from the compliance zone designators. When an individual is within a compliance zone, his/her wearable device receives the transmitted signal and recognizes that a compliance zone has been established in the area. Once a compliance zone has been recognized, the wearable device identifies any criteria there may be for interacting with the compliance zone as specified by the protocol being enforced. The wearable device may optionally provide real-time reminders or alerts to notify the wearer of the protocol criteria. The wearable device then determines if the individual is in compliance with the criteria. The wearable device logs the result of the determination and processes information relating to the criteria. Compliance may include assessment of how the individual interacts with items in the area, such as a hand-washing station. The logged compliance data may be accessed, downloaded, reviewed or analyzed in a variety of ways to determine the effectiveness of the enforcement. The logged compliance data may optionally be used to set off real-time alerts.

FIGS. 1 through 21, wherein like parts are designated by like reference numerals throughout, illustrate example embodiments of a system and method for enforcing protocols relating to use of and/or interactions with compliance zones, according to exemplary embodiments. Although exemplary embodiments will be described with reference to the figures, it should be understood that many alternative forms can embody the present invention. One of ordinary skill in the art will additionally appreciate different ways to alter the parameters of the embodiments disclosed, such as the size, shape, or type of elements or materials, in a manner still in keeping with the spirit and scope of the present invention.

I. System

FIG. 1 depicts an exemplary embodiment of a system 100 for establishing a compliance zone and monitoring interactions therewith. The system 100 includes a compliance zone designator 110 and a wearable device 120 separate from the compliance zone designator 110. In use, the compliance zone designator 110 establishes a compliance zone 130. When the wearable device 120 is within the compliance zone 130, a compliance zone recognition component 140 of the wearable device recognizes the compliance zone 130, and identifies one or more interaction criteria associated with the compliance zone 130. Based on the interaction criteria, the wearable device 120 operates according to the needs of the interaction criteria. In addition, the wearable device 120 may determine and record compliance with the interaction criteria. Each of the elements of the system 100, including their operation and interaction with other elements, are discussed in more detail below.

II. Compliance Zone Designator

The system 100 includes the compliance zone designator 110. The compliance zone designator 110 establishes or designates the compliance zone 130 by, for example, transmitting a signal. As such, the compliance zone designator 110 may be configured for placement at a location where a compliance zone 130 is desired. A compliance zone 130 may be established anywhere the enforcement of protocols is desired. For example, a compliance zone 130 may be used for patients, beds, rooms, equipment, or the like. As such, the compliance zone designator 110 is designed for easy placement at a number of locations, e.g. attached to persons, equipment, locations, etc. The compliance zone designator 110 may also be mobile and may be moved to change the location of compliance zone designated by the designator 110.

The compliance zone designator 110 may be turned on or off at will.

Figure 2:
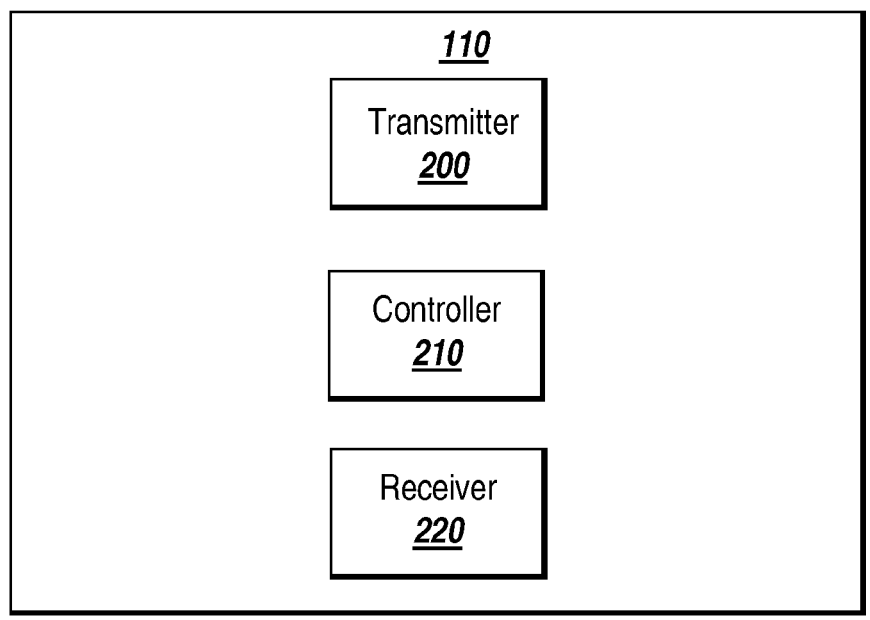
FIG. 2 depicts a block diagram of an exemplary embodiment of a compliance zone designator.

FIG. 2 depicts an exemplary embodiment of a compliance zone designator 110. In this embodiment, the compliance zone designator 110 includes a transmitter 200, a controller 210, and a receiver 220. The transmitter 200 transmits an ultrasound signal to establish the compliance zone. The range of the signal transmitted by the transmitter 200 establishes the outer limits of the compliance zone 130, unless there are obstructions that limit the signal as later discussed. In some embodiments, the compliance zone designator 110 may include multiple transmitters.

The controller 210 is programmed to control the transmitter 200, the transmitted ultrasound signal, and the receiver 220. The controller 210 may be any type of controller, microcontroller, processor, or microprocessor suitable that is programmed to control a transmitter 200. The controller 210 may dictate what type of signal the transmitter 200 transmits, or may dictate variations in how the signal transmits. The signal transmitted by the transmitter 200 to establish the compliance zone may be a unique, semi-unique, non-unique signal or any combination thereof. For example, a unique signal may be used in correlation with a specific patient, while a semi-unique signal may be used with a type of patient. In some embodiments, an identification number and/or other information, such as date and time information, is encoded in the ultrasound signal. The transmission of the signal may be continuous, periodic, in response to a signal received at the compliance zone designator 110, or any combination thereof. The type of signal as well as signal strength may be user specified using the controller 210.

The controller 210 is also programmed to control the transmitter 200 such that the ultrasound signal transmitted by the transmitter 200 is encoded by data. The data may include, but is not limited to, information on the type and identity of the compliance zone established by the ultrasound signal, information on the compliance zone designator 110, etc.

In certain embodiments, the compliance zone designator 110 further includes a receiver 220. The receiver 220 is configured to receive ultrasound signals at the compliance zone designator 110. In some embodiments, the receiver 220 may be used to receive signals for configuring the compliance zone designator 110. In certain embodiments, the receiver 220 may be used in conjunction with the transmitter 200 and controller 210 to form a transponder that transmits a signal in response to a signal received at the compliance zone designator 110. In some such embodiments, the range and/or type of signal transmitted may be determined by the signal received by the receiver 220.

Figure 3:
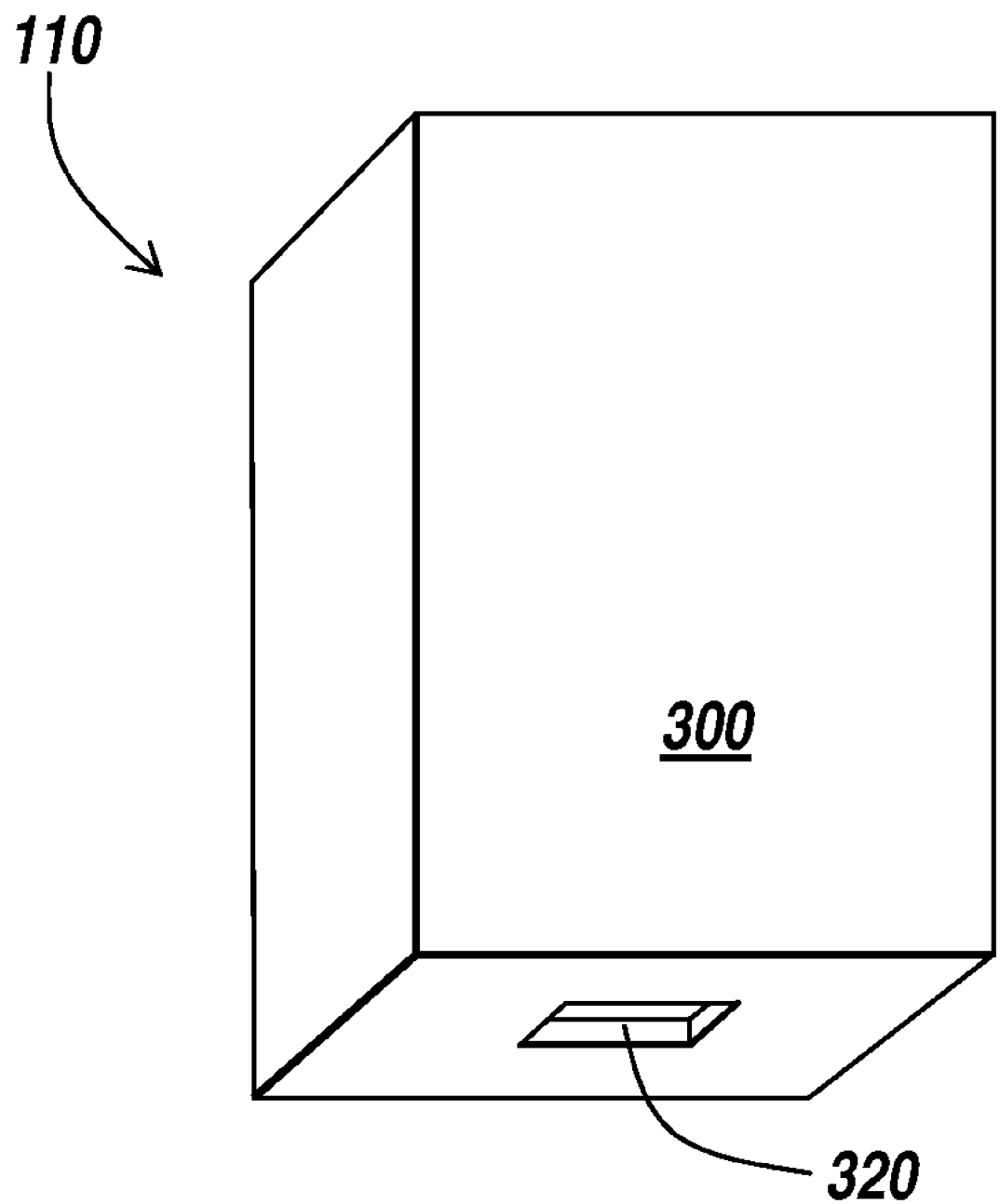
FIG. 3 depicts a perspective view of the exemplary protective zone designator of FIG. 2.

FIG. 3 depicts an exemplary embodiment of a compliance zone designator 110 configured for placement at a location where a compliance zone is desired. The compliance zone designator 110 may include a housing 300 for housing the transmitter 200, controller 210, and the receiver 220. The housing may be formed of plastic, metal, or other suitable materials. The housing may be sized and dimensioned to allow for easy placement of the compliance zone designator 110 at a number of locations and for movement of the compliance zone designator 110 from one location to another. In certain embodiments, the compliance zone designator 110 may be battery-powered. In other embodiments, the compliance zone designator 110 may plug into a wall socket, or be hardwired into a power source or grid.

In some embodiments, the compliance zone designator 110 may further include a data port 320 for the transfer of data to and from the compliance zone designator 110. The data port 320 may be used to communicate with the controller 210 to configure the compliance zone designator 110. Examples of a suitable data ports include a serial port, such as a universal serial bus (USB) port, or an Ethernet port. Other possible ports will be apparent to one skilled in the art given the benefit of this disclosure. In other embodiments, the transmitter 200 and receiver 220 of the compliance zone designator 110 are used to transmit data back and forth from the compliance zone designator 110.

III. Wearable Device

The system 100 also includes the wearable device 120. The wearable device 120 is separate from the compliance zone designator 110 with which it interacts at any specific compliance zone. Typically, in use, a user wears the wearable device 120 to track the wearer's interactions with the compliance zone 130. The wearable device 120 includes a compliance zone recognition component 140 configured to recognize the compliance zone 130 and identify one or more pre-defined interaction criteria for the compliance zone 130. An exemplary embodiment of a compliance zone recognition component 140 is depicted in FIG. 4.

Figure 4:
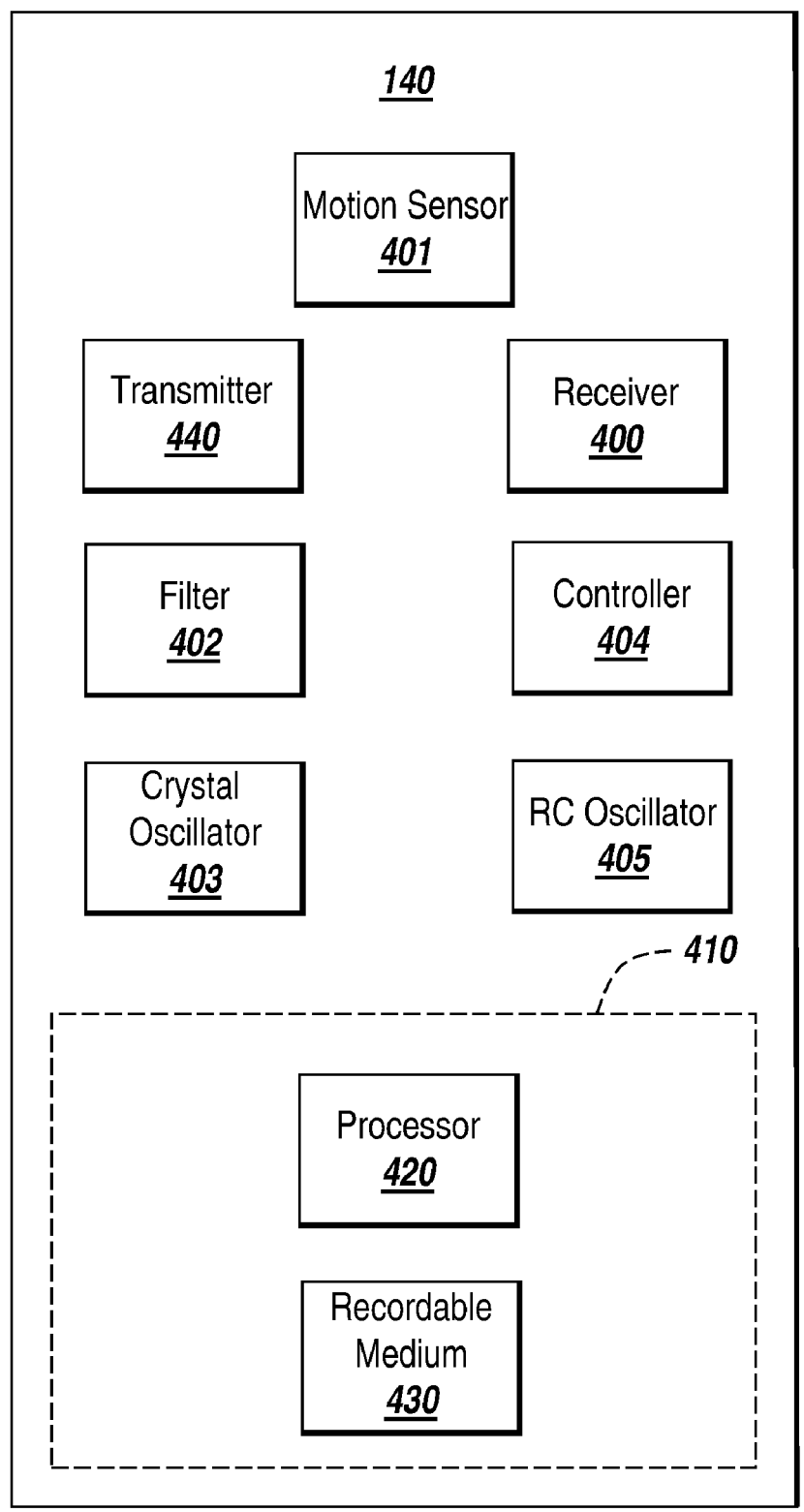
FIG. 4 depicts a block diagram of an exemplary embodiment of a wearable device useable.

In the exemplary embodiment depicted in FIG. 4, the compliance zone recognition component 140 includes a receiver 400, a filter 402, a controller 404, a transmitter 440, and a computing device 410.

The receiver 400 is a suitable acoustic-to-electric transducer or sensor, e.g. a microphone, optimized to receive signals in the ultrasound frequency range, such as the signal transmitted from a compliance zone designator 110. The electric signals corresponding to the acoustic signals received by the receiver 400 are filtered by an RC circuit filter 402 within the compliance zone recognition component 140. The RC circuit filter 402 allows only those signals corresponding to the ultrasound frequency range to pass through.

The receiver 400 is configured to operate at low power even though the receiver listens for ultrasound signals at all times. The controller 404 is programmed to control the operation of the processor 420, and is normally kept off during the operation of the wearable device 120. The controller 404 and the processor 420 are turned on only when the filter 402 detects signals corresponding to the ultrasound frequency range, lets these signals through the filter 402, and outputs these signals. The controller 404 and the processor 420 are kept off at other times, e.g. when the receiver 400 receives audible sounds which do not establish compliance zones. This selective activation of the controller 404 and the processor 420 reduces the power the wearable device 120 would otherwise consume.

Power is also consumed to maintain a high-accuracy crystal oscillator 403 that acts as the clock of the controller 404. In order to minimize power consumption by the controller clock, the timing of the controller 404 is kept using a lower-accuracy RC or LC oscillator 405 built into the controller 404, instead of the high-accuracy crystal oscillator 403. The RC or LC oscillator 405 timer is based on the charging and discharging of a capacitor through a resistor or currents source. The accuracy of the RC or LC oscillator 405 is lower than the crystal oscillator 403, and thus the system must be able to tolerate some margin of error. Thus, the filter 402 allows in received signals of carrier frequencies above or below 2% of the ideal frequency.

To further reduce power consumption in the wearable device 120, the wearable device 120 may be equipped with a motion sensor 401 that detects whether the wearer of the device is moving or stationary. A wearer who is standing stationary is not likely to receive new information on compliance zones in his/her vicinity. Upon the motion sensor 401 detecting that the wearer is stationary, the controller 404 may turn off the components of the wearable device 120 that consumer power, e.g. the filter 402 and the processor 420. The controller 404 may subsequently turn on the components when the motion sensor detects that the wearer has started to move.

Preferably, the receiver 400 is of the same type as the transmitter 200 in the compliance zone designator 110, which allows the wearable device to receive a transmission from the compliance zone designator 110 designating a compliance zone. In some embodiments, the wearable device 120 may include multiple receivers that may be of different types. In some embodiments, the receiver 400 may be used to receive signals for configuring the wearable device 120. For example, predetermined or pre-defined criteria for a compliance zone 130 may be configured by a signal received at the wearable device 120. Likewise, the wearable device 120 can be configured to be associated with a particular user wearing the wearable device 120. For example, each wearable device 120 may have a unique identification number that can be associated with a particular user.

The computing device 410 includes a processor 420 and a recordable medium 430. The processor 420 may be any suitable processor capable of interfacing with the receiver 400 and programmed to process signals received by the receiver to recognize a compliance zone 130, identify pre-defined interaction criteria for the compliance zone 130, determine compliance with the interaction criteria, and record whether or not there is compliance with the interaction criteria. Suitable processors will be apparent to one skilled in the art given the benefit of this disclosure. The recordable medium 430 is used to store instructions for the processor 420, including interaction criteria, and data obtained or generated by the processor 420, including compliance with the interaction criteria. Such data may include the date, time, and result, of any interaction with a compliance zone 130. The recordable medium 430 may be a memory device, that is provided integrally with or separate from the wearable device 120. Other suitable recordable mediums will be apparent to one skilled in the art given the benefit of this disclosure.

In an exemplary embodiment, the ultrasound signal received at the receiver 400 is encoded with data. In this embodiment, the processor 420 of the wearable device 120 is programmed to process the received ultrasound signal and decode the data encoded in the ultrasound signal.

In some embodiments, the compliance zone recognition component 140 may further include one or more transmitters 440. The one or more transmitters 440 are configured to transmit ultrasound signal from the wearable device 120. In accordance with some embodiments of the present invention, the wearable device may include multiple transmitters.

In certain embodiments, the one or more transmitters 440 may be used in conjunction with the receiver 400 in a transponder configuration. In such a configuration, the one or more transmitters 440 transmits a query signal to the receiver 220 of the compliance zone designator 110 that in turn transmits a signal in response from the transmitter 200 of the compliance zone designator 110. In some such embodiments, the signal transmitted by the one or more transmitters 440 of the compliance zone recognition component 140 determines the range and/or type of signal transmitted by the compliance zone designator 110.

Figure 5A:
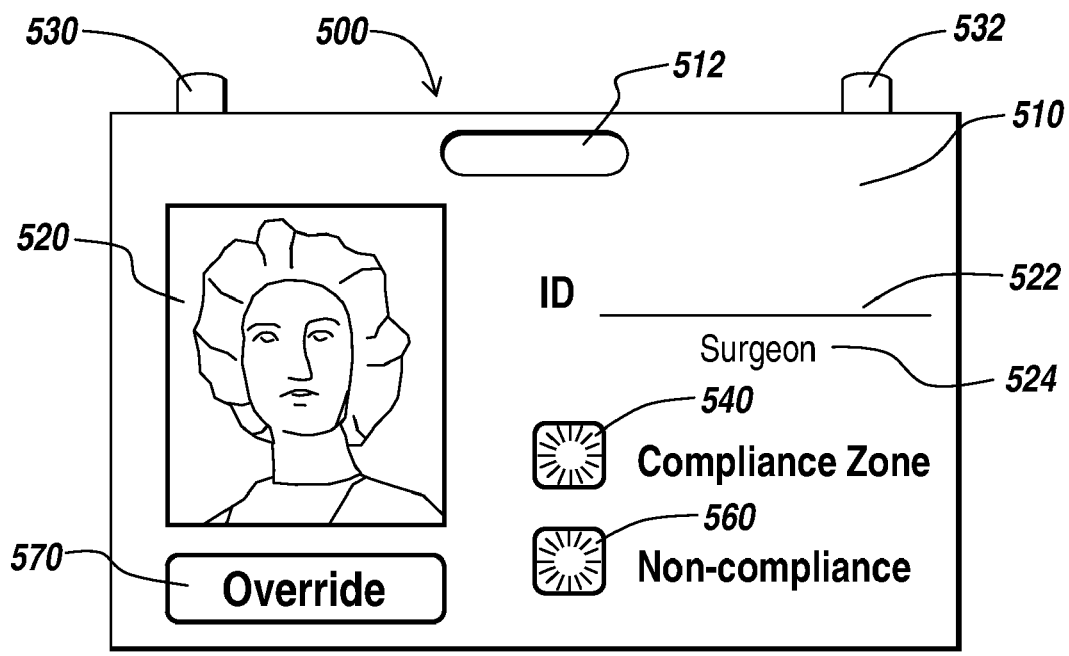
FIG. 5A depicts a front perspective view of an exemplary wearable device wherein the wearable device is a badge.
Figure 5B:
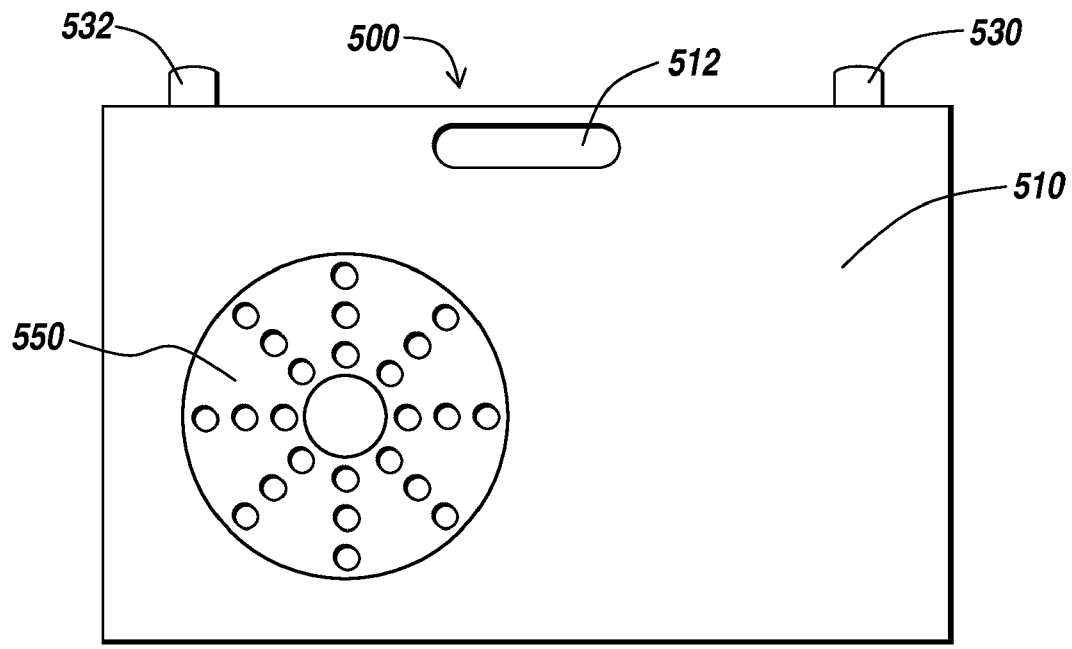
FIG. 5B depicts a back view of the badge of FIG. 5A.

FIGS. 5A and 5B depict an exemplary embodiment of a wearable device 120, wherein the wearable device is a badge 500. The badge may be in the form of the standard institution-specific identification badge. FIG. 5A depicts a front view of the badge 500. FIG. 5B depicts a back view of the badge 500.

The badge 500 includes a housing 510 containing the compliance zone recognition component 140. The housing 510 includes a thru-hole 512 for attaching a clip or lanyard to the badge 500. The housing 510 may be made of plastic or other suitable materials. On the front of the badge 500, the identification information for the wearer of the badge may be provided. This may include a photograph 520 of the person associated with the badge, as well as the name 522 and position 524 of the associated person. In embodiments, the badge 500 may further include an external receiver 530 and/or an external transmitter 532. Preferably, a battery, such as a rechargeable or replaceable battery, powers the badge 500. In some embodiments, the badge 500 may include a port, such as a USB or Ethernet port that may be used for data transfer and charging the battery.

In certain embodiments, the wearable device 120 is capable of providing notice of the compliance zone upon entering or when inside the compliance zone. The notice may be audible, visual, tactile, or any combination thereof. In the example of FIGS. 5A and 5B, a visual notice is provided by a light-up indicator 540 such as a light emitting diode (LED) on the front side of the badge 500 as shown in FIG. 5A. An audible notice or alarm is provided by a speaker 550 provided on the back side of the badge 500 as shown in FIG. 5B. A tactile notice may be provided by vibration.

In some embodiments, the wearable device 120 may additionally provide notice that the wearer of the badge does not comply with the interaction criteria for a compliance zone. When the wearable device enters into a non-compliance mode, the notice of non-compliance may be audible, visual, or tactile. In the example of FIGS. 5A and 5B, a visual notice is provided by a light-up indicator 560 such as a light emitting diode (LED) on the front side of the badge 500 as shown in FIG. 5A. An audible notice is provided by the speaker 550 provided on the back side of the badge 500 as shown in FIG. 5B. A tactile notice may be provided by vibration.

In some embodiments, an override is provided on the wearable device 120. The override allows the user to turn off the notice of non-compliance provided by the wearable device 120. The override may be a button or a switch 570 provided on the badge 500 allowing the user to select the override. In some embodiments, the override may be provided by software executed on the wearable device 120. The availability of the override may also depend on the identity or role of the wearer of the wearable device. That is, certain wearers of a wearable device might not have the option of an override available to them. For example, in a hospital environment, doctors may have the option of an override while housekeeping staff may not. In some such embodiments, the use of an override may be recorded on the wearable device 120 or elsewhere on the system.

Figure 6A:
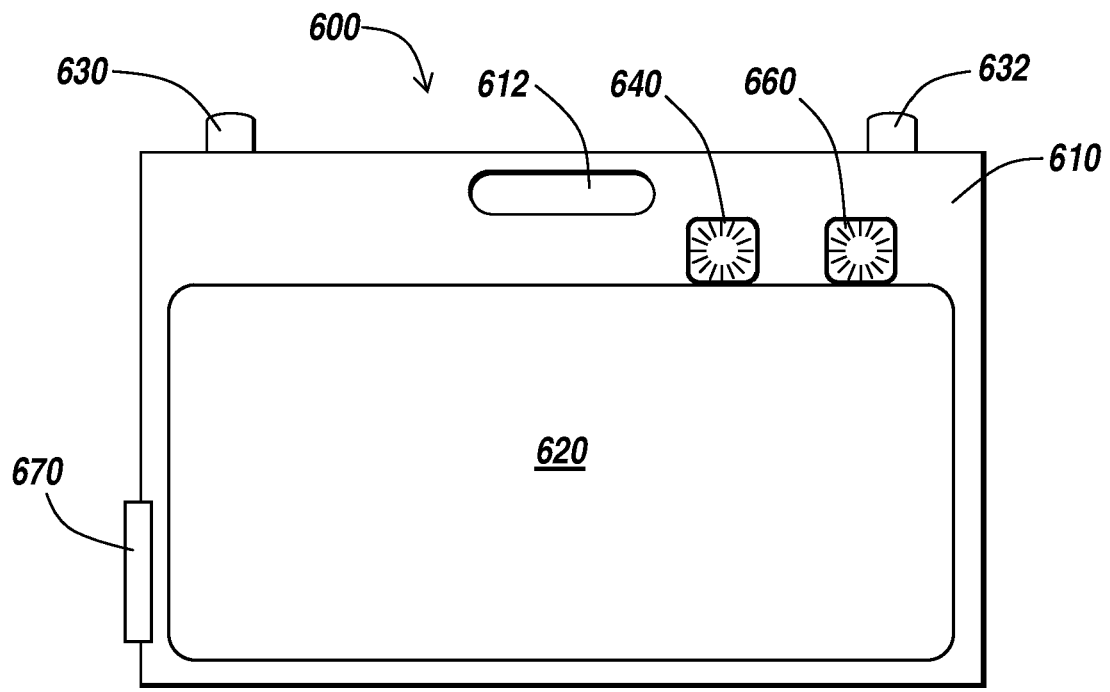
FIG. 6A depicts a front perspective view of an exemplary wearable device wherein the wearable device is a badge-holder.
Figure 6B:
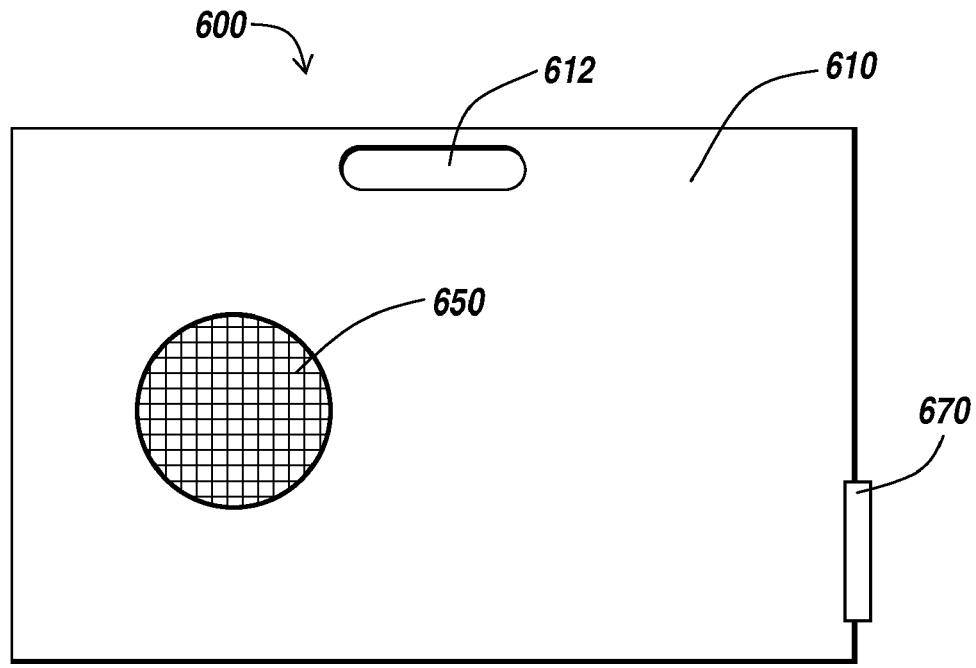
FIG. 6B depicts a back view of the badge-holder of FIG. 6A.

FIGS. 6A and 6B depict one exemplary embodiment of a wearable device wherein the wearable device is a badge holder 600 wherein the wearable device is configured to attach to a standard institution-specific identification badge. FIG. 6A depicts a front view of the badge holder 600. FIG. 6B depicts a back view of the badge holder 600.

Similar to the badge 500 of FIGS. 5A and 5B, the badge holder 600 includes a housing 610 containing the compliance zone recognition component 140. The housing 610 includes a thru-hole 612 for attaching a clip or lanyard to the badge holder 600. The housing 610 may be made of plastic or other suitable materials. The badge holder 600 pairs with a traditional identification badge. The badge holder 600 has an area 620 designed to receive and hold an identification badge. Preferably, the badge holder 600 may be powered by a battery, such as a rechargeable or replaceable battery. In some embodiments, the badge 500 may include a port, such as a USB or Ethernet port that may be used for data transfer and charging the battery.

As with the badge 500 of FIGS. 5A and 5B, the badge holder 600 may provide notice that the badge holder 600 has entered into a compliance zone 130 or is within a compliance zone 130. The notice may be audible, visual, tactile, or any combination thereof. In the example of FIGS. 6A and 6B, a visual notice is provided by a light-up indicator 640 such as a light emitting diode (LED) on the front side of the badge holder 600 as shown in FIG. 6A. An audible notice is provided by a speaker 650 provided on the back side of the badge holder 600 as shown in FIG. 6B. A tactile notice may be provided by vibration.

The badge holder 600 may also provide notice that the wearer of the badge does not comply with the interaction criteria for a compliance zone. The notice of non-compliance may be audible, visual, tactile, or any combination thereof. In the example of FIGS. 6A and 6B, a visual notice is provided by a light-up indicator 660 such as a light emitting diode (LED) on the front side of the badge holder 600 as shown in FIG. 6A. An audible notice is provided by the speaker 650 provided on the back side of the badge holder 600 as shown in FIG. 6B. A tactile notice may be provided by vibration.

The badge holder 600 may also be provided with an override functionality. The override may be a button or a switch 670 provided on the badge holder 600 allowing the user to select the override. The availability of the override may depend on the identity or role of the wearer of the wearable device. In some such embodiments, the use of an override may be recorded on the badge holder 600.

IV. Data Encoding in Ultrasound Signals

The ultrasound signals which are used to establish a compliance zone may be encoded with data. The data may include, but is not limited to, information on the type and identity of the compliance zone established by the ultrasound signal, information on the compliance zone designator 110, etc. Each compliance zone designator encodes its ultrasound signal transmission with the data. The controller of the compliance zone designator is programmed to control the transmitter of the compliance zone designator such that the ultrasound signal transmitted by the transmitter is encoded with the data.

In an exemplary embodiment, data encoded in the ultrasound signal transmitted by a compliance zone designator identifies a specific compliance zone. The data may be in the form of a message. In this embodiment, the message is encoded in the timing between successive bursts of ultrasound carrier cycles.

Each compliance zone designator transmits a message including an assigned zone ID at regular intervals. The zone ID may uniquely identify a specific compliance zone. For example, the zone ID transmitted by all hand-washing stations may have a particular value, e.g. 0. Other compliance zone designators may have zone IDs with values 1 through 1023. In exemplary embodiments, more than one compliance zone designator may be assigned the same zone ID. However, duplicate zone IDs are not assigned to nearby compliance zones that someone wearing a wearable device 120 could move between within a minute.

Figure 7:
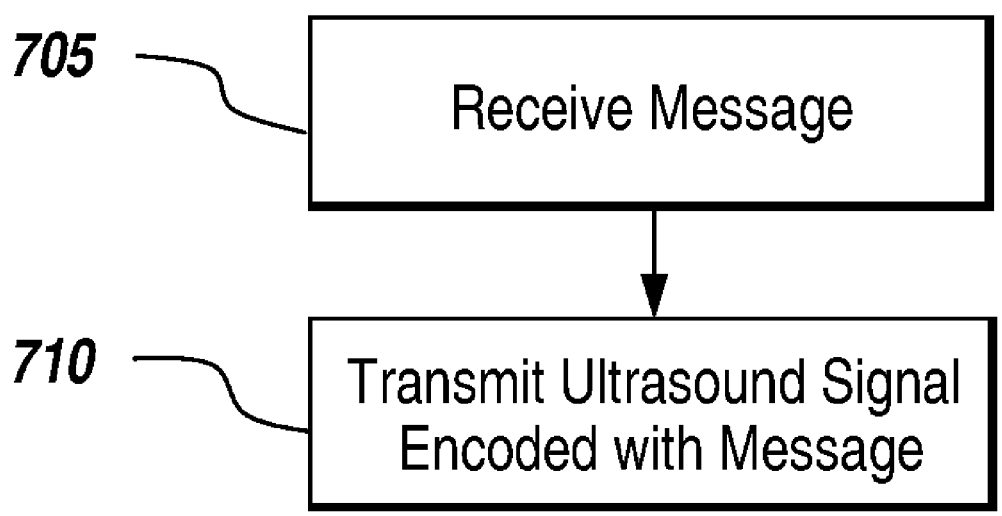
FIG. 7 is a flowchart of one exemplary embodiment of a methodology for establishing a compliance zone.

FIG. 7 is a flowchart of one exemplary embodiment of a methodology for establishing a compliance zone. The compliance zone designator receives a 15-bit message to be encoded in the ultrasound signal that establishes the compliance zone (step 705). Alternatively, the compliance zone designator generates the message based on the zone ID associated with the compliance zone and a cyclic redundancy check (CRC) checksum associated with the zone ID. In this embodiment, the compliance zone designator may receive the zone ID and/or the CRC checksum, or determine these values itself. The compliance zone designator generates the 15-bit message by setting the high 10 bits of the message to the zone ID and the low 5 bits of the message to the CRC checksum.

The compliance zone designator then establishes the compliance zone by transmitting an ultrasound signal using an ultrasound transmitter (step 710). The compliance zone designator encodes the ultrasound signal with the 15-bith message which includes the zone ID uniquely identifying the compliance zone. The message is encoded in the sequence of time intervals between consecutive bursts of the ultrasound signal. More specifically, the compliance zone designator periodically transmits 7 bursts of the ultrasound signal, with each burst being a sequence of 6 carrier cycles. The message is encoded in the 6 time intervals between consecutive bursts in the 7 bursts of the ultrasound signal, such that each nominal time interval corresponds to a particular character of the message.

Exemplary implementations of data encoding in ultrasound signals are layered into pulses, bursts, characters, and messages which will now be described.

Pulse: A "pulse" denotes an input received by a processor decoding an ultrasound signal, the input indicating that one ultrasound carrier cycle has been received. In an exemplary embodiment, the ultrasound carrier frequency is about 40 KHz, at which a pulse occurs every 25 microseconds when the carrier is on. The carrier frequency may be derived from a low-cost and low-power RC or LC timer oscillator built into the controller of the compliance zone designator. The RC or LC timer oscillator is not highly accurate and, therefore, the system is capable of tolerating some margin of error. As such, in an exemplary embodiment, ultrasound receivers receiving the ultrasound pulses expect that the carrier frequency is within 2% of the ideal frequency, 40 KHz, as the pulses arrive at the receivers.

Other errors can accumulate before the ultrasound pulses are ultimately received at the ultrasound receiver and processed by firmware in the receiving processor. These errors include inherent jitter in the ultrasound amplifier of the transmitter and inherent jitter in the receiver. Additional jitter is caused by quantizing the time to integer cycles of a reference clock and by sampling data in the firmware. To accommodate for these and other errors, in an exemplary embodiment, the system allows for up to 8% error in the receiving firmware, i.e. in the ultrasound receiving processor. That is, in an exemplary embodiment, the receiving firmware interprets the time intervals between pulses as being valid if the time intervals are between 23 and 27 microseconds, inclusive.

Burst: A "burst" denotes a sequence of pulses in which all the time intervals between consecutive pulses are within a valid range, i.e. are between 23 and 27 microseconds, inclusive, in the above exemplary embodiment. The valid time intervals between consecutive pulses in a burst indicate that the pulses were likely the result of receiving ultrasound at the carrier frequency.

Figure 8A:
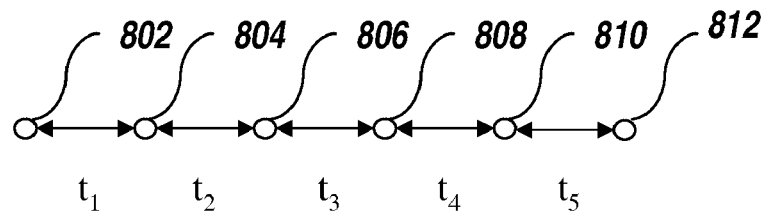
FIG. 8A depicts the pulses in an exemplary embodiment of a burst of ultrasound signal.

In an exemplary embodiment illustrated in FIG. 8A, a burst 800 is detected when 6 successive pulses (802-812) with valid time intervals ($t_1$-$t_5$) are received. A time interval between consecutive pulses is valid if the time interval is between 23 and 27 microseconds, inclusive. Due to the resonance of the ultrasound transmitters and receivers, the first couple of carrier cycles may be received at lower amplitudes and, therefore, possibly not be received at all. The ultrasound transmitters thus transmit at least 8 carrier cycles per burst. However, increasing the number of carrier cycles per burst lengthens the time that the ultrasound signal persists in the environment, and increases the possibility of the signal echoing from surfaces and being received with a delay. In order to prevent reception of delayed signals, the ultrasound transmitters do not transmit more than 10 carrier cycles per burst. That is, the ultrasound transmitters transmit 8 to 10 carrier cycles per burst.

After receiving a valid burst of the ultrasound signal, the ultrasound receivers ignore additional pulses for a blackout period in order to minimize or eliminate multipath interference in the ultrasound signals. Multipath interference is a phenomenon whereby a wave from a source travels to a detector via two or more paths and, under certain conditions, the two or more components of the wave interfere. The ultrasound signals echo around the environment and could be received multiple times at a single receiver. The minimum valid time interval between bursts is chosen such that the echo from the previous burst has died down. In an exemplary embodiment, the absolute minimum valid time interval between bursts is 32.23 milliseconds. The blackout period is set so that it expires at least in time to receive the first pulse in the next burst, including the margin for all possible sources of error in the system. In an exemplary embodiment, the minimum blackout time is 30 milliseconds, which corresponds to about 10 meters of propagation distance. In exemplary embodiments, any desired blackout time can be selected and used to configure the ultrasound receiver.

Character: Characters are the constituent components of a message transmitted by a compliance zone designator. A "character" denotes the data encoded in the single time interval between two consecutive bursts. There is a limited range of valid time intervals between two consecutive bursts. Valid characters fall within this valid range, with each unique character corresponding to a predefined, nominal time interval between two consecutive bursts. Time intervals falling outside the valid range do not correspond to any characters.

Exemplary embodiments provide 9 valid characters: start-of-message (SOM) and integer values 0 through 7. The SOM character corresponds to a nominal time interval of 1/32 seconds (31.25 milliseconds). Additional characters correspond to time interval increments of 1/512 seconds (1.953 milliseconds) added to the SOM time interval, with the 0 character being the first and the 7 character the last. That is, the SOM character time is 1/32 seconds (31.25 milliseconds), the 0 character is 1/32+1/512 seconds, the 1 character is 1/32+2/512 seconds, the 2 character is 1/32+3/512 seconds, the 3 character is 1/32+4/512 seconds, the 4 character is 1/32+5/512 seconds, the 5 character is 1/32+6/512 seconds, the 6 character is 1/32+7/512 seconds, and the 7 character is 1/32+8/512 seconds (46.88 milliseconds).

There is no illegal time between valid character times. In the above exemplary embodiment, a time interval is first rounded to the nearest multiple of 1/512 seconds to interpret the character encoded in the time interval. That is, the valid time interval associated with each character is the nominal time interval±1/1024 seconds (±977 microseconds). Therefore, the range of valid character times is between the minimum possible SOM character (1/32−1/1024 seconds=30.27 milliseconds) and the maximum possible 7 character (1/32+8/512+1/1024 seconds=47.85 milliseconds). Burst time intervals outside this range are invalid.

Message: A "message" denotes at least the zone ID along with a cyclic redundancy check (CRC) checksum associated with the zone ID. The zone ID may be an identifier associated with a compliance zone that indicates the type of the compliance zone (e.g. operating room, hand washing station, etc) and/or may be a unique identifier associated with the compliance zone (e.g. operating room number 14, hand washing station 43, etc). The CRC checksum is a number that is used to determine the validity of the message, e.g. to determine whether the message has been altered during transmission of the ultrasound signal.

A message is a specific sequence of characters. The size of the message thus depends on the number of characters in the message. Each character is encoded in a single time interval between two consecutive bursts of ultrasound signal. Thus, the size of the message is determined by the number of bursts that incorporate the message. That is, the larger the number of bursts that form a message, the larger the message.

A suitable message size and a corresponding number of bursts are selected for use in exemplary embodiments. The compliance zone designator transmits the ultrasound signal according to the number of bursts per message, periodically. In a very large facility with a need for a very large number of zone IDs, the message size and the number of bursts per message may be very large as well. On the other hand, in a small facility, the message size and the number of bursts per message may be smaller.

Figure 8B:
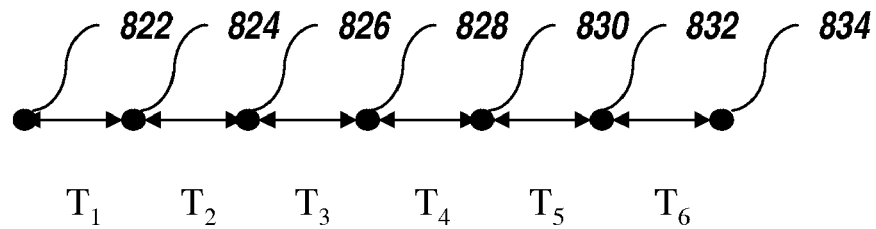
FIG. 8B depicts the bursts in an exemplary embodiment of a message of ultrasound signal.

In an exemplary embodiment illustrated in FIG. 8B, a message 820 is a specific sequence of 6 valid characters in succession, the characters corresponding to 6 nominal time intervals between consecutive bursts within 7 bursts in succession (822-834). The first character is the SOM (start-of-message) character, and the remaining characters are data characters (0-7). Each character is encoded in a single time interval between two consecutive bursts in the message ($T_1$-$T_6$). Thus, the message is encoded in the sequence of time intervals between consecutive bursts within the 7 valid bursts.

Figure 8C:
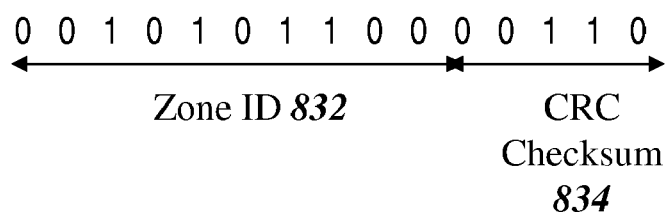
FIG. 8C depicts the message bits in an exemplary embodiment of a message of ultrasound signal.

As illustrated in FIG. 8C, a message 830 contains 15 bits of information, the 10 most significant bits of the message corresponding to the zone ID 832, and the 5 least significant bits of the message corresponding to the CRC checksum 834 for the zone ID.

Since all messages begin with an SOM character and this character does not appear otherwise, a received SOM character is always interpreted as the start of a new message. So, when an SOM character is received, the previous message is discarded. This guarantees that the start of a message can always be recognized regardless of what sequence of pulses precedes the start of the message. That is, an ultrasound receiver is always "listening" for the start of a message regardless of where the receiver thinks it is within a message.

A complete message is only received if the above-described rules for valid pulses, bursts, characters and messages are adhered to over the whole message. A message is discarded immediately if any of these rules is broken over the message.

If a rule violation is detected at the pulse or burst level, the message interpretation logic is reset. That is, the message is discarded, and the next pulse received is assumed to be the first pulse of the first burst of a message.

The last burst of a message may also be the first burst of the next message. That is, after a complete message is received, the message interpretation logic is reset to expecting the next burst to end an SOM character, not starting an SOM character.

Figure 9:
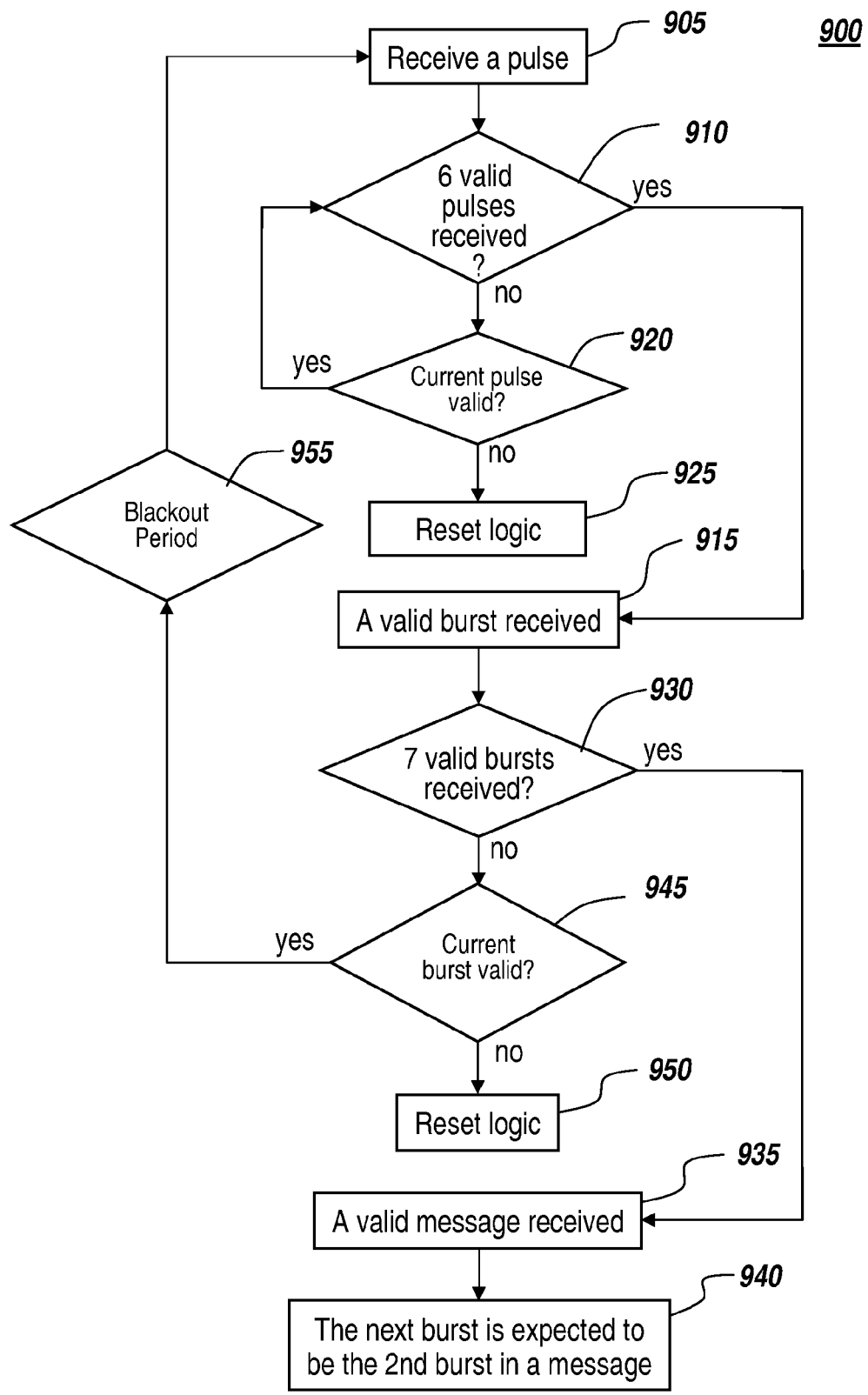
FIG. 9 is a flowchart of an exemplary message interpretation logic used in decoding a message encoded in an ultrasound signal.

FIG. 9 depicts a flow chart 900 of one example embodiment of message interpretation logic used to decode a message encoded in an ultrasound signal. The message interpretation logic may be followed by a wearable device in decoding a message encoded in an ultrasound signal that is received at the wearable device. A processor of the wearable device is programmed to process the received ultrasound signal and decode the data encoded in the ultrasound signal.

A pulse of ultrasound signal is received at an ultrasound receiver (step 905). If 6 valid pulses have been received (step 910), then a valid burst of ultrasound signal has been received (step 915). However, if 6 valid pulses have not been received (step 910), then the message interpretation logic determines whether the current pulse is valid (step 920). If the current pulse is the first pulse in the burst, then the current pulse is considered valid. However, if the current pulse is not the first pulse in the burst, then the pulse is valid only if the time interval between the current pulse and the immediately previous pulse is between 23 and 28 microseconds. If the current pulse is not valid, then the message interpretation logic is aborted (step 925). That is, the next received pulse is assumed to be the first pulse of the first burst of a new message. However, if the current pulse is valid, then the next pulse is received (step 910).

If 6 valid pulses have been received, then a valid burst of ultrasound signal has been received (step 915). If 7 valid bursts have been received (step 930), then a valid message has been received (step 935). In this case, the immediately subsequent burst is expected to be the second burst in a new message (step 940).

However, if 7 valid bursts have not yet been received (step 930), then the message interpretation logic determines whether the current burst is valid (step 945). If the current burst is the first burst in the message, then the current burst is considered valid. If the current burst is the second burst in the message, then the current burst is valid only if the time interval between the current burst and the immediately previous burst corresponds to the SOM character, i.e. is 1/32±1/1024 seconds. If the current burst is the third to seventh burst in the message, then the current burst is valid only if the time interval between the current burst and the immediately previous burst corresponds to a data character (0-7).

If the current burst is not valid, then the message interpretation logic is aborted (step 950). The next received pulse is assumed to be the first pulse of the second burst of a new message. However, if the current burst is valid, then the next pulse in the next burst of the message is received after a blackout period (step 955). The blackout period is at least 30 milliseconds from the time the current pulse was received during which no further pulses are received. That is, the next pulse is received at least 30 milliseconds after the current pulse was received.

Message validation: As illustrated in FIG. 8C, the low 5 bits of each 15-bit message is a cyclic redundancy check (CRC) checksum 834. A CRC is a non-secure hash function designed to detect accidental changes to the raw zone ID 832 transmitted in the ultrasound signal. The compliance zone designator calculates a short, fixed-length binary sequence, known as the CRC checksum, for each zone ID. The compliance zone designator creates a 15-bit message by setting the low 5 bits of the message to the CRC checksum and the high 10 bits of the message to the zone ID. Thus, the ultrasound signal transmitted by the compliance zone designator is encoded with a message containing both the zone ID and the CRC checksum.

Figure 10:
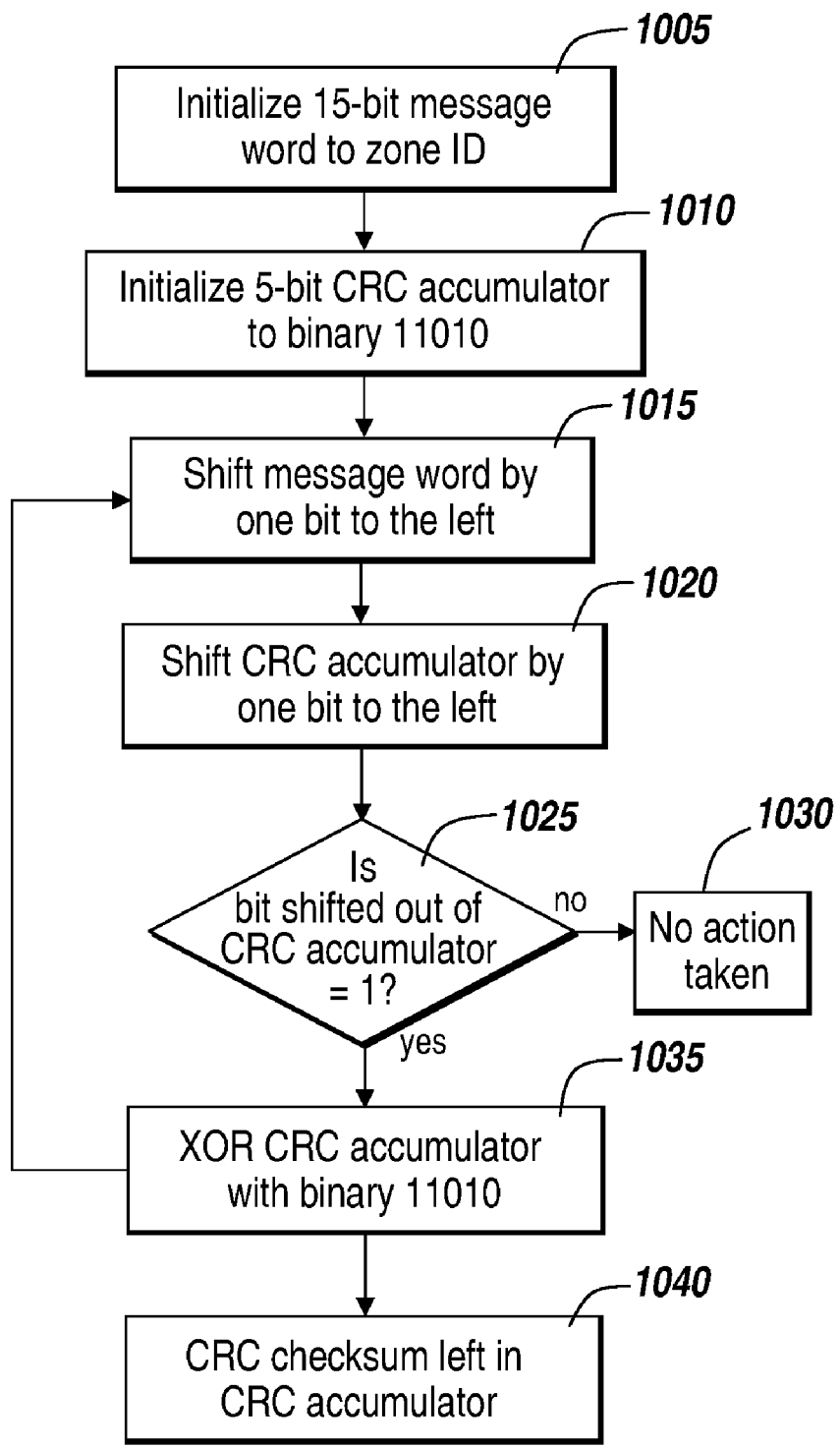
FIG. 10 is a flowchart of an exemplary method of calculating a cyclic redundancy check (CRC) checksum of a message.

FIG. 10 is a flowchart of an exemplary method of calculating a CRC checksum of a message. This method may be followed by a compliance zone designator to determine a CRC checksum to incorporate into a message that is encoded in an ultrasound signal. A 15-bit message word is initialized to the zone ID (step 1005). A 5-bit CRC accumulator is initialized to binary 11010 (step 1010). The message word is shifted by one bit to the left, and the bit shifted out of the most significant bit is saved (step 1015). The CRC accumulator is shifted by one bit to the left (step 1020). The bit shifted into the least significant bit of the CRC accumulator is the bit shifted out of the most significant bit in step 1015, and the bit shifted out of the most significant bit of the CRC accumulator is saved. If the bit shifted out of the CRC accumulator in step 1020 was 1 (step 1025), then the CRC accumulator is XOR'ed with binary 11010 (step 1035). Otherwise, if the bit shifted out of the CRC accumulator in step 1020 was 0, then no action is performed (step 1030). Steps 1015-1035 are repeated once for each of the 14 remaining message bits. At the end of the procedure, the CRC checksum is left in the CRC accumulator (step 1040).

When a wearable device receives the ultrasound signal, the wearable device processes the signal to decode the message. The wearable device extracts the zone ID from the high 10 bits of the message and calculates a new CRC checksum corresponding to the message. If the new CRC checksum calculated by the wearable device is non-zero, the message contains a data error and the wearable device discards the message. However, if the new CRC checksum calculated by the wearable device is zero, the message is free of errors and the wearable device extracts the zone ID from the high 10 bits of the message. The CRC checksum bits of the message are no longer necessary and are discarded at this point.

Figure 11:
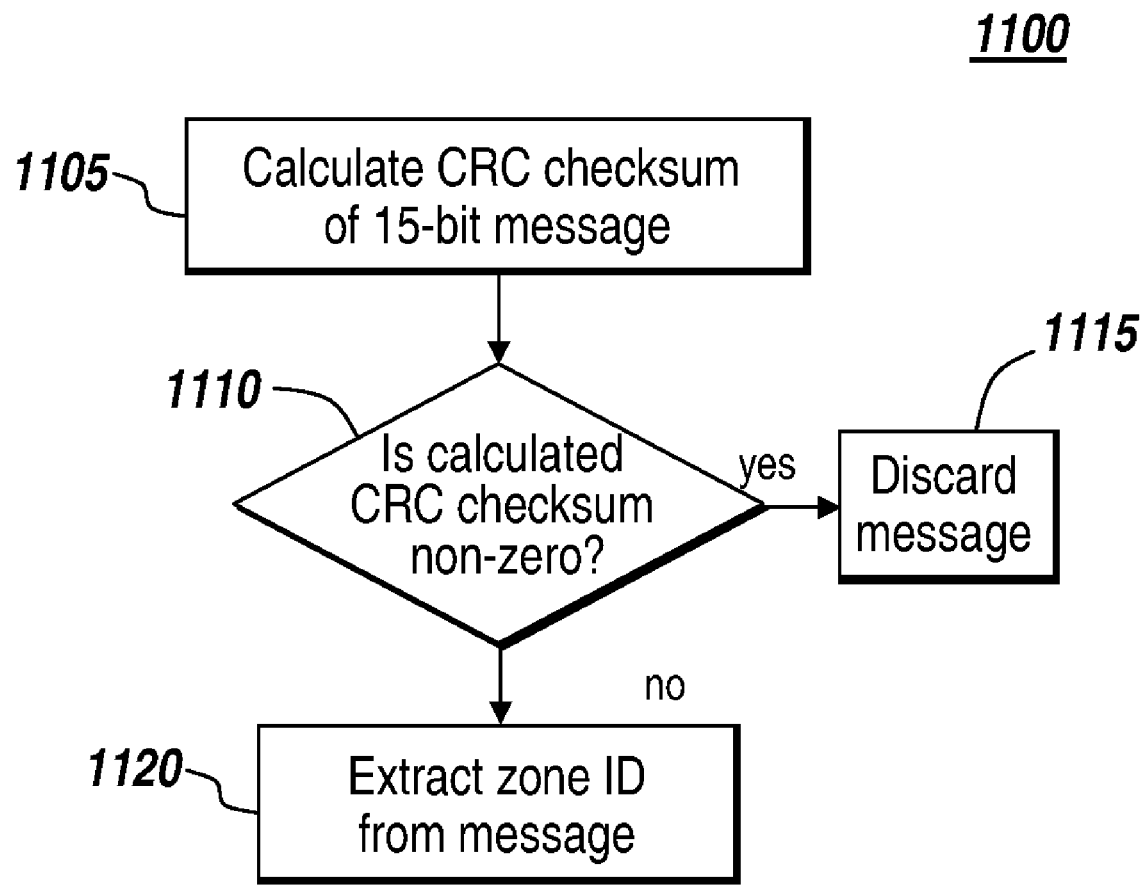
FIG. 11 is a flowchart of an exemplary method of determining the validity of a message using a CRC checksum.

FIG. 11 is a flowchart of an exemplary method of determining the validity of a message using a CRC checksum. This method may be followed by a wearable device that receives an ultrasound signal establishing a compliance zone. The CRC checksum of the 15-bit message is calculated, e.g. based on the methodology depicted in FIG. 10 (step 1105). If the calculated CRC checksum is 0 (step 1110), then the message is considered valid, i.e. without errors (step 1120). In this case, the zone ID is then extracted from the high 10 bits of the message, and the low 5 bits are discarded (step 1120). However, if the calculated CRC checksum is not 0 (step 1110), then the message is considered invalid, i.e. with errors (step 1115). In this case, the message is discarded (step 1115).

V. Interaction Criteria

As discussed previously, upon recognizing a compliance zone 130, the compliance zone recognition component 140 of the wearable device 120 identifies the interaction criteria for the compliance zone 130. The interaction criteria may be the rules or requirements for interacting with the compliance zone. For example, a compliance zone 130 may be provided for an area containing hazardous material. Thus, the interaction criteria for the compliance zone 130 could be that the wearer is trained or otherwise certified to handle hazardous materials. In another example, a compliance zone 130 could be provided for a classified area. Thus, the interaction criteria for the compliance zone 130 could be security clearance above a certain level.

In accordance with some embodiments of the present invention, the interaction criteria for a compliance zone 130 may include temporal requirements. For example, in the example of the hazardous material area, there may be time limits for safe exposure to the hazardous material. In other embodiments, there may be a time limit for compliance with the interaction criteria. For example, a wearer of the wearable device within the compliance zone 130 must complete a requirement within a certain amount of time. In still other embodiments, the interaction criteria themselves may be derived based on the time of day. For example, in the evenings there may be lockdown of the facility for security purposes. In other words, a compliance zone 130 may have one set of interaction criteria during the day and another set of interaction criteria during the evening, or some other combination of different criteria throughout a 24 hour period, or based on day, month, or even year.

In some embodiments, the interaction criteria may be biohazard requirements and/or notification. For example, a compliance zone 130 may be provided for an area where virus research is conducted. The interaction criteria may include a general warning that the area contains biohazards as well as requirements that persons within the compliance zone 130 undertake safety precautions such as using a hazardous material suit.

In one example embodiment of the present invention, the interaction criteria may be certification requirements. For example, a compliance zone 130 may be provided for a highly contagious patient at a hospital. Thus, the interaction criteria for the compliance zone 130 may be certification in infectious medicine.

In certain embodiments, the identity or role of the user wearing the wearable device may factor into the interaction criteria for a compliance zone 130. For example, in a hospital setting, the interaction criteria derived by the compliance zone recognition component 140 may be different for a doctor than for a housekeeper. Likewise, individual doctors may have different interaction criteria for the same compliance zone 130.

In accordance with some embodiments of the present invention, the interaction criteria may also include requirements upon exiting the compliance zone 130. For example, if the compliance zone 130 is provided for a biohazard zone, the interaction criteria may include a requirement that the wearer of the wearable device visit a decontamination area after leaving the compliance zone 130.

The interaction criteria may be configurable in allowing for any number of implementations, configurations, requirements, and/or permutations to serve a number of applications. In some such embodiments, the ability configure the interaction criteria may be restricted wherein access to configure the interaction criteria may require authorization, authentication, or both. For example, it may be desirable for only administrators to be able to configure interaction criteria. In other embodiment, different users may have different privileges for configuring interaction criteria.

Figure 12:
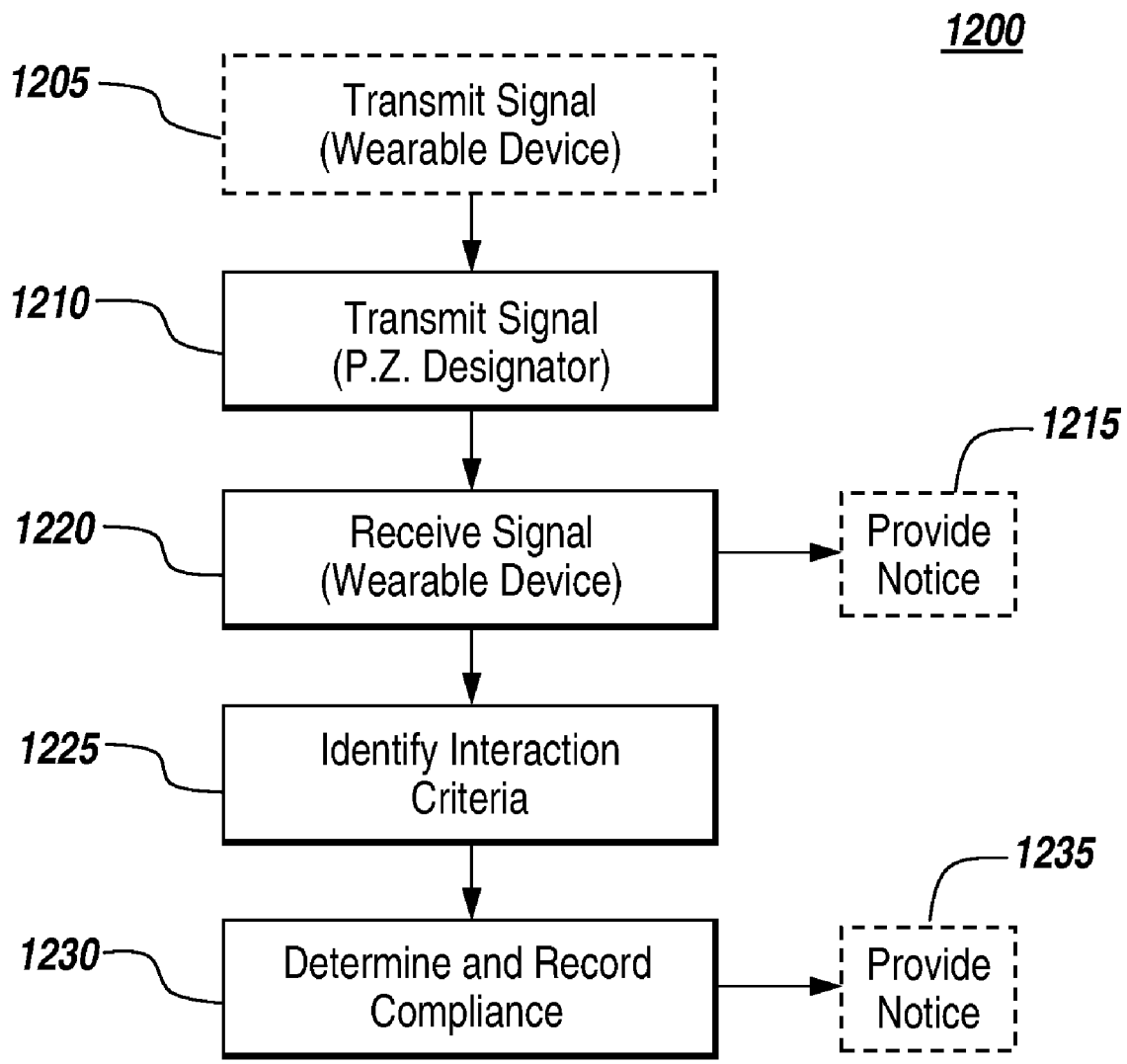
FIG. 12 is a flowchart of an exemplary method of for establishing a compliance zone and monitoring interactions therewith.

FIG. 12 is a flowchart 1200 of an exemplary method of for establishing a compliance zone and monitoring interactions therewith. For example, the depicted method can be implemented with the system depicted in FIG. 1. The method begins with the compliance zone designator 110 transmitting a signal (step 1210). The transmission of the signal defines the compliance zone 130. In certain embodiments, the signal is transmitted from the compliance zone designator 110 in response to a signal from the wearable device 120 (step 1205). The wearable device 120 receives the signal when the wearable device 120 is within the compliance zone 130 (step 1220). In certain embodiments, the wearable device 120 may provide notice that the compliance zone 130 has been entered or that the wearable device 120 is within the compliance zone 130 (step 1215). For example, a warning, such as an audible, visual, and/or tactile warning may be provided. Since the wearable device 120 is worn by the user, any such indications or warnings can be provided subtly and directly to the user, without requiring additional infrastructure. Such subtle and direct indications or warnings to a particular user minimize alarm to all patients or customers present in the vicinity of the wearable device 120. The communication capabilities of the wearable device 120 also allow the user to interact with the wearable device 120.

The compliance zone recognition component 140 of the wearable device 120 then processes the received ultrasound signal to decode information encoded in the ultrasound signal. For example, the information may include the type and/or identity of the compliance zone established by the ultrasound signal. The compliance zone recognition component 140 identifies the interaction criteria for the compliance zone, based on the information encoded in the received ultrasound signal (step 1225). The compliance zone recognition may then act in accordance with the interaction criteria, e.g. provide a real-time indication to the wearer of the requirements of the interaction (e.g. by flashing a light or beeping), or transmit and/or receive ultrasound signals to comply with the interaction criteria. The compliance zone recognition component 140 of the wearable device 120 determines and records compliance with the identified interaction criteria (step 1230). In certain embodiments, the wearable device 120 may also provide notice of non-compliance (step 1235). For example, a warning or alarm, such as an audible, visual, and/or tactile warning may be provided.

VI. Hospital Example Featuring Hand-Washing Requirements

For greater understanding of the concepts set forth herein, the following example of a system deployed in a specific facility for a specific purpose is provided. The example deployment is in a hospital and is purposed with enforcing barrier protection requirements, e.g. hand washing, gloving, sanitizing, etc. For simplicity, this example will now be described with reference to hand washing. However, the capabilities of the system extend to any type of barrier protection requirements.

Figure 13:
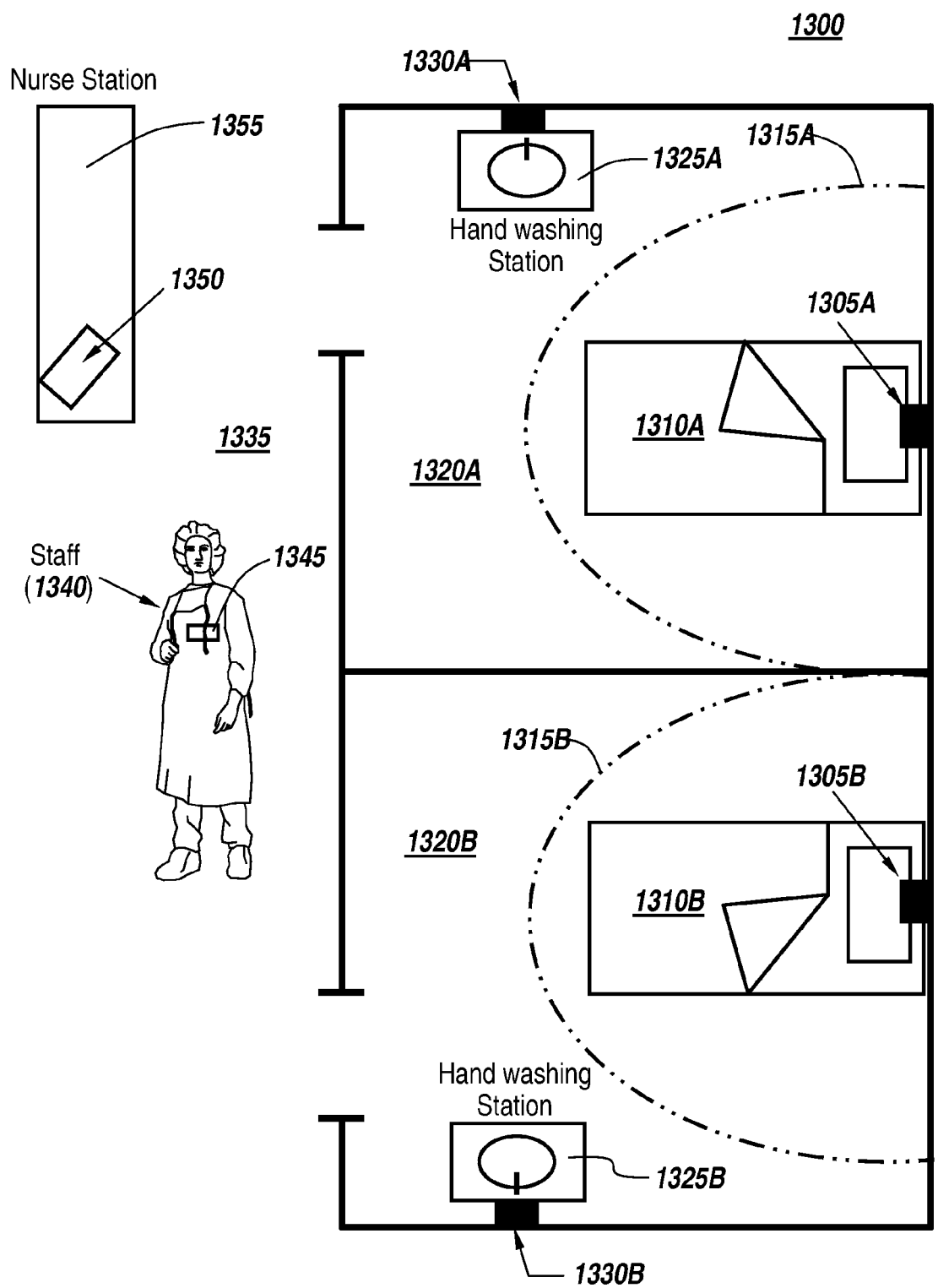
FIG. 13 depicts an exemplary embodiment of a system for enforcing hand washing requirements in a hospital.

FIG. 13 depicts an exemplary embodiment of a system for enforcing hand washing requirements in a hospital. However, it should be noted that the present invention is in no way limited to the specific examples described herein. These examples are merely provided for illustrative purposes.

In FIG. 13, the system 1300 has been deployed in a hospital environment. In this embodiment, the system 700 includes multiple compliance zone designators 1305A and 1305B and a wearable device 1345. In this embodiment, the system 1300 further includes a base station 1350, and multiple hand washing stations 1325A and 1325B.

The hand washing stations 1325A and 1325B may be sinks supplying water and soap, hand sanitizer dispensers, or the like, used to clean, sanitize, and/or disinfect an individual's hands. The hand washing stations 1325A and 1325B include transmitters 1330A and 1330B respectively. Transmitters 1330A and 1330B are configured to transmit data, such as a signal indicating that the respective hand washing station 1325A or 1325B has been used. The transmitters 1330A and 1330B are ultrasound transmitters. In accordance with some embodiments of the present invention, there may be multiple transmitters that may be of different types, so long as transmitters 1330A or 1330B transmit in a signal type that can be received by the wearable device 1345. In accordance with some embodiments of the present invention, the hand washing stations 1325A and 1325B may further be equipped with receivers (not shown) allowing for a transponder configuration in which a signal is sent from the hand washing stations 1325A and 1325B in response to a query signal sent from the wearable device 1345. As with the transmitters, the receivers are ultrasound receivers. In some such embodiments, the transmitters 1330A or 1330B may also be used in conjunction with the receivers in a transponder configuration.

In the present example, the compliance zone designators 1305A and 1305B are placed to provide compliance zones 1315A and 1315B around patient beds 1310A and 1310B in rooms 1320A and 1320B respectively. Rooms 1320A and 1320B also contain hand washing stations 1325A and 1325B respectively.

A hospital staff member 1340 such as a doctor or a nurse wears the wearable device 1345. In the embodiment of FIG. 13, the staff member 1340 is in the corridor 1335 outside of the rooms 1320A and 1320B. The corridor 1335 also contains a nurse's station 1355 where the base station 1350 is located.

To enforce hand washing requirements, the system 1300 is configured such that, when a hospital staff member 1340 (wearing the wearable device 1345) enters a compliance zone 1315A or 1315B, a determination is made by the wearable device 1345 whether the hospital staff member 1340 has washed his or her hands just prior to entering the compliance zone 1315A or 1315B. If the hospital staff member 1340 has washed their hands, the wearable device 1345 will record the compliance with the hand washing requirement. If the hospital staff member 1340 has not washed his/her hands, the wearable device 1345 will issue a warning or prompt that compliance with the hand washing requirements is required. As mentioned above with regard to the badge 500 and badge holder 600 embodiments, the warning or prompt may be audible, visual, tactile, or any combination thereof. After the warning has been issued, the hospital staff member 1340 may activate an override, wash their hands in response to the warning, or not wash their hands in response to the warning. If the override is activated, the wearable device 1345 records that the override was activated. If the hospital staff member 1340 washes their hands in response to the warning, the wearable device 1345 records that the wearer's hands were washed after the warning was issued. If, after a pre-selected amount of time (e.g. 30 seconds) the hospital staff member 1340 does not wash their hands in response to the warning, then the wearable device 1345 records their non-compliance with the hand washing requirement.

In order for the wearable device 1345 to be able to determine if the hospital staff member 1340 has washed their hands, the wearable device 1345 is provided with a hand washing monitor configured to record interactions with hand washing stations 1325A and 1325B.

Figure 14:
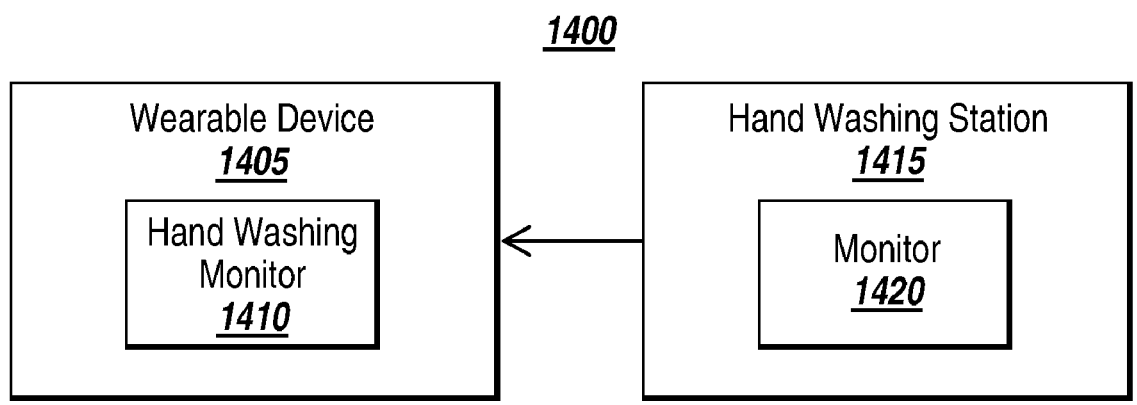
FIG. 14 depicts a block diagram of one portion of the system of FIG. 13.

FIG. 14 depicts a block diagram of one portion of the system of FIG. 13. More specifically, FIG. 14 depicts an exemplary embodiment of a system 1400 having a wearable device 1405 and a hand washing station 1415 configured to interact with each other. The wearable device 1405 includes a hand washing monitor 1410 configured to keep track of interactions with the hand washing station 1415. The hand washing station 1415 may also include a monitor 1420 that keeps track of the use of the hand washing station 1415.

The monitor 1420 of the hand washing station 1415 may be configured to track the use of the hand washing station. For example, if the hand washing station is a sink, the monitor 1420 may track the use of the faucet and the soap dispenser. If the hand washing station 1415 is a hand sanitizer dispenser, then the monitor 1420 may track the use of the dispenser. If the monitor 1420 detects that the hand washing station 1415 has been used, then the monitor 1420 may direct the hand washing station to transmit a signal, such as a "wash stamp" indicating that the hand washing station was used. In certain embodiments, the signal transmitted may be unique. For example, a "wash stamp" transmitted by the hand washing station 1415 may include an identification number for the hand washing station 1415. The "wash stamp" may also include other information, such as time and date.

In some embodiments wherein the hand washing station 1415 has a transponder configuration, the monitor 1420 may wait for a signal received from the wearable device 1405 before a signal indicating use is sent in response. In some embodiments, the monitor 1420 may record each use of the hand washing station 1415. In embodiments having a transponder configuration, the recorded data may include the identification information for the wearable device 1405 interacting with the hand washing station 1415. The recorded data may then be accessed and reviewed.

The hand washing monitor 1410 of the wearable device 1405 may be part of a compliance zone recognition component 140 as set forth above, or it may be separate from the compliance zone recognition component 140. The hand washing monitor 1410 may be configured to receive the signals received from the hand washing station 1415. For example, the hand washing monitor 1410 may log or otherwise record "wash stamps" generated by the monitor 1420 of the hand washing station 1415 and data pertaining to the received "wash stamp." Data pertaining to the "wash stamp" may include the identification number of the hand washing station 1415 from which the "wash stamp" was received as well as the time and date the "wash stamp" was received. This data may then be used to determine compliance with hand washing requirements. For example, to determine if the hospital staff member has washed their hands, the data recorded by the hand washing monitor 1410 may be consulted to indicate, among other things, whether a "wash stamp" has been received, when it was received, and from which hand washing station 1415 it was received.

As mentioned previously, the interaction criteria may include a temporal aspect. In the hand washing example of FIGS. 13 and 14, the temporal aspect may include how long ago a signal or "wash stamp" indicating a hand washing was received prior to entering the compliance zone 1315A or 1315B. For example, if the last received "wash stamp" was received more than 15 seconds prior to entering the compliance zones 1315A and 1315B, chances are that the hands of the hospital staff member 1340 are no longer sanitary. In that case the wearable device 1345 may be configured to require a more recent "wash stamp" to comply with the hand washing requirement of the compliance zones 1315A and 1315B. Likewise, the wearable device 1345 may record how long it took to receive a "wash stamp" after the wearable device 1345 issued a warning or prompt indicating the need for the hospital staff member 1340 to wash their hands.

In exemplary embodiments, the interaction criteria implementing the hand washing requirements also require the hospital staff member 1340 to wash their hands after exiting the compliance zones 1315A or 1315B. For example, the wearable device 1345 may require that a new "wash stamp" be received within a pre-selected amount of time (e.g. 30 seconds) after exiting the compliance zone to prevent the possible spread of infection. If a new "wash stamp" is not received within the allotted period a warning or prompt may be issued. The warning or prompt may be audible, visual, tactile, or any combination thereof. After the warning has been issued, the hospital staff member 1340 may activate an override, wash their hands in response to the warning to receive a new "wash stamp," or not wash their hands in response to the warning. If the override is activated, the wearable device 1345 records that the override was activated. If the hospital staff member 1340 washes their hands in response to the warning, the wearable device 1345 records that the "wash stamp" was received after the warning was issued. If, after a pre-selected amount of time, the hospital staff member 1340 does not wash their hands in response to the warning, then the wearable device 1345 records their non-compliance with the hand washing requirement.

The determination of compliance with the interactive criteria depends on the requirements or protocols implemented by the interactive criteria. For example, in the embodiment of FIGS. 13 and 14, the interactive criteria were used to implement hand washing requirements. To determine if a hospital staff member 1340 washed their hands, "wash stamps" were used. One embodiment of a methodology for implementing this system can be seen in FIG. 15.

Figure 15:
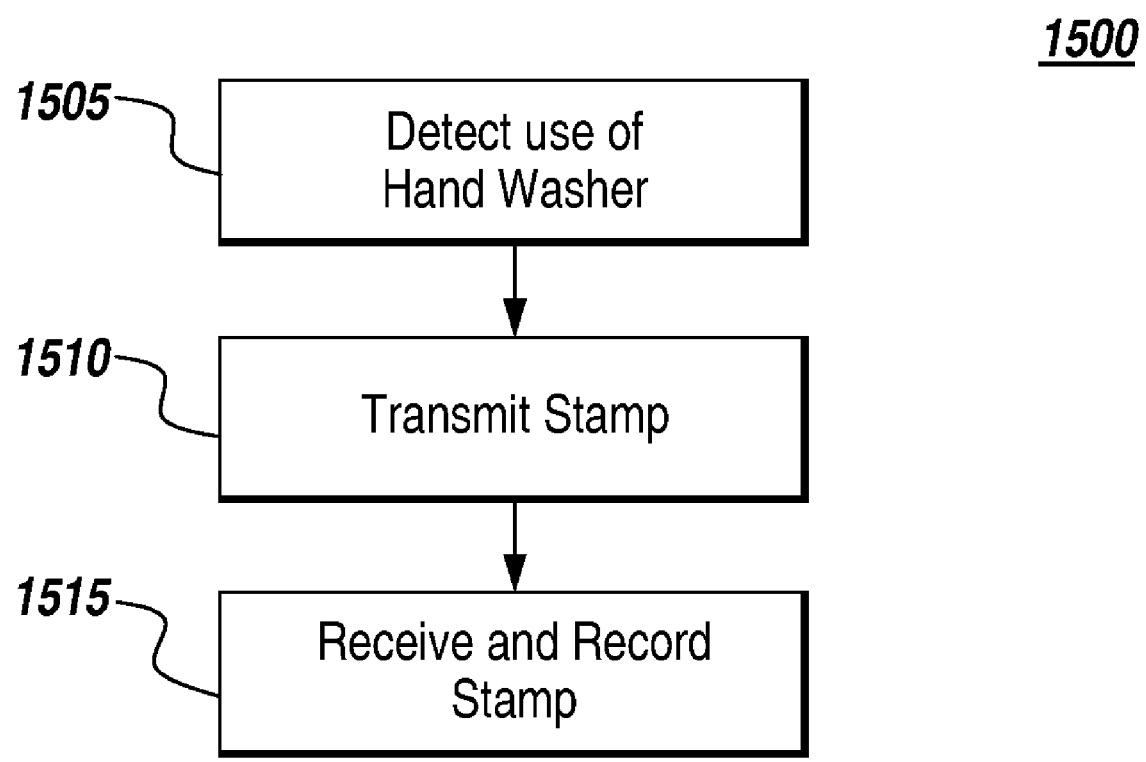
FIG. 15 is a flowchart of an exemplary method of interactions between a wearable device and hand-washing stations as depicted in FIG. 14.

FIG. 15 depicts a flow chart 1500 of an exemplary embodiment of a method of the interaction between the wearable device 1405 and hand washing stations 1415 depicted in FIG. 14. First, it is determined if hand washing station 1415 has been used (step 1505). This may be done by the monitor 1420 of the hand washing station. Then a signal, such a "wash stamp," indicating that hand washing station has been used is transmitted (step 1510). The "wash stamp" is then received and recorded at the wearable device 1405 indicating the hospital staff member has washed their hands (step 1515). In certain embodiments, this may be performed by hand washing monitor 1410 of the wearable device 1405.

Figure 16:
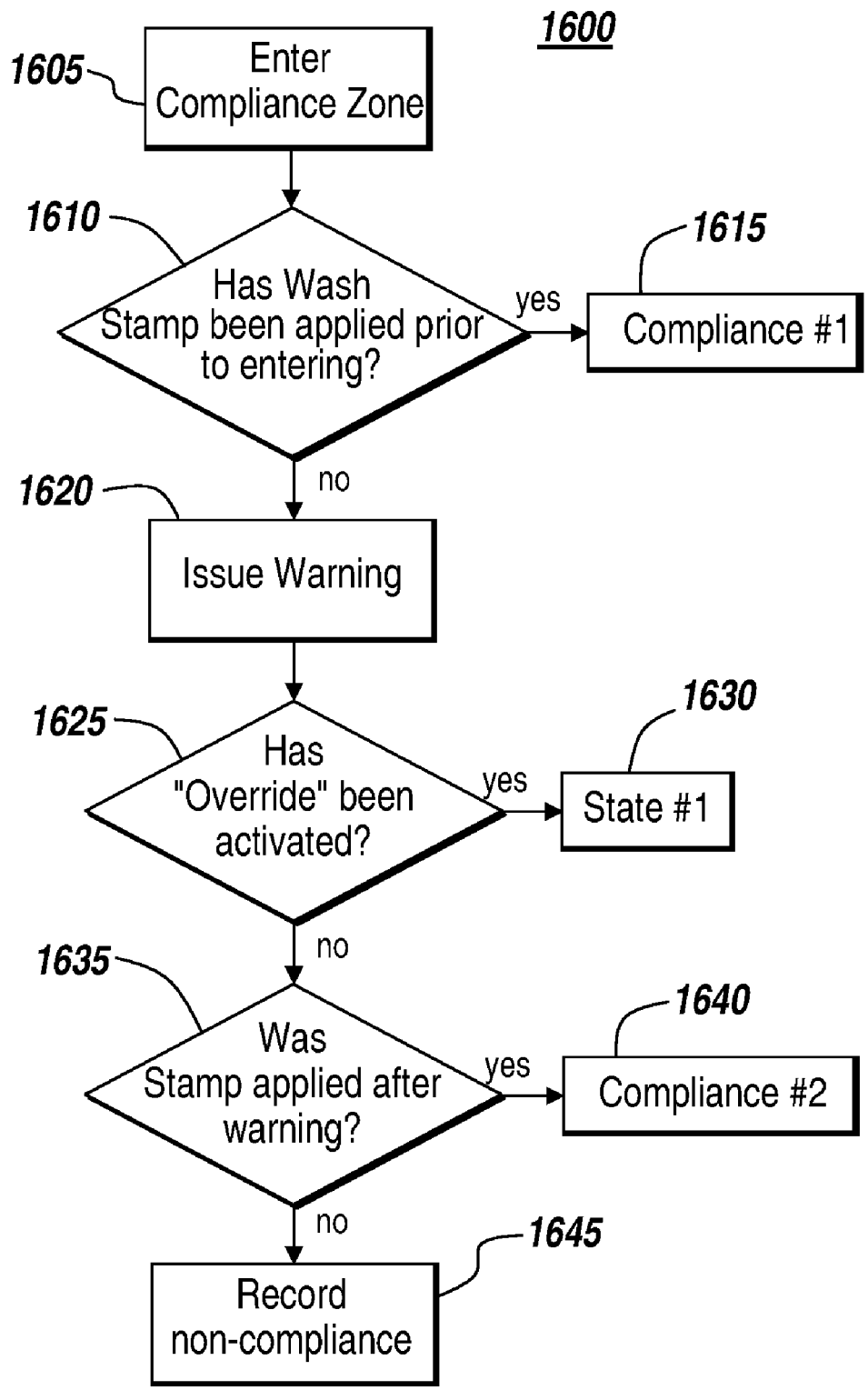
FIG. 16 is a flowchart of an exemplary method for enforcing hand-washing requirements in a hospital.

FIG. 16 depicts a flow chart 1600 of an exemplary method for enforcing hand-washing requirements in a hospital. This method may be practiced using the system of FIG. 14. A hospital staff member enters one of the compliance zones 1315A and 1315B (step 1605). It is then determined if a "wash stamp" was received by the wearable device 720 prior to entering the compliance zone 1315A or 1315B (step 1610). If a "wash stamp" was received, the wearable device 1405 records a satisfactory entry (Compliance #1") (step 1615). If a "wash stamp" was not received prior to entering the compliance zone 1315A or 1315B, the wearable device issues a warning (step 1620). The wearable device then determines if the override has been activated (step 1625). If the override was activated, the wearable device 1405 records the activation ("State 1") (step 1630). If the override was not activated, the wearable device 1405 determines if a "wash stamp" was received after the warning (step 1635). If a "wash stamp" was received, then the wearable device 1405 records a satisfactory entry (Compliance #2") (step 1640). If a "wash stamp" was not received then the non-compliance is recorded (step 1645).

Figure 17:
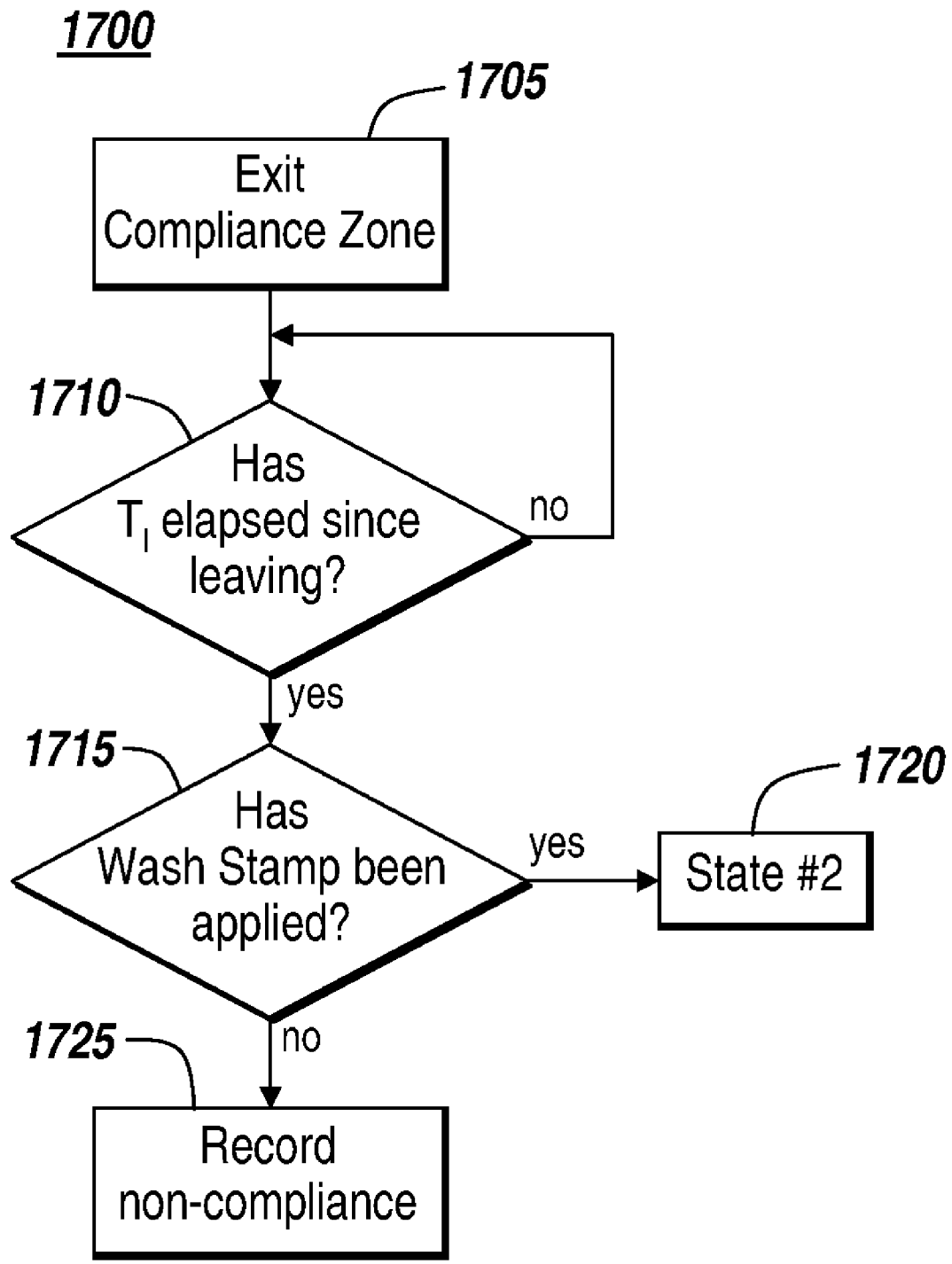
FIG. 17 is a flowchart of an exemplary method for enforcing hand-washing requirements in a hospital after leaving the compliance zones.

FIG. 17 depicts a flow chart 1700 of an exemplary method for enforcing hand-washing requirements in a hospital after leaving the compliance zones. The hospital staff member exits one of the compliance zones 1315A and 1315B (step 1705). It is then determined if time $T_1$ has elapsed since leaving the compliance zones 1315A and 1315B (step 1710). For example, time $T_1$ may be 30 seconds. It is then determined if a "wash stamp" was received prior to time $T_1$ elapsing (step 1715). If a "wash stamp" was received, the wearable device 1405 records a satisfactory entry ("State 2") (step 1720). If a "wash stamp" was not received prior to time $T_1$ elapsing, the wearable device 1405 will record the non-compliance (step 1725).

VII. Hospital Example Featuring Timeout Protocol

Another exemplary use of the system in accordance with the present invention is in recording and enforcing a timeout protocol in an operating room before the beginning of a surgical procedure. During a timeout protocol, good practice dictates that all hospital staff participating in the surgical procedure, e.g. surgeon, nurses, anesthetist, etc, pause to make sure that the correct patient is about to get the correct surgical procedure. During a timeout protocol, a staff-member announces the start of the protocol and reads aloud the patient's name and details of the surgical procedure. The timeout protocol prevents avoidable surgical errors by allowing a hospital staff-member to speak up if he/she does not agree on the patient's identity or on the details of the surgical procedure. Timeout protocols are difficult to enforce in practice, as staff-members often continue to work during the protocol and fail to pay attention to the information read out during the protocol.

Figure 18:
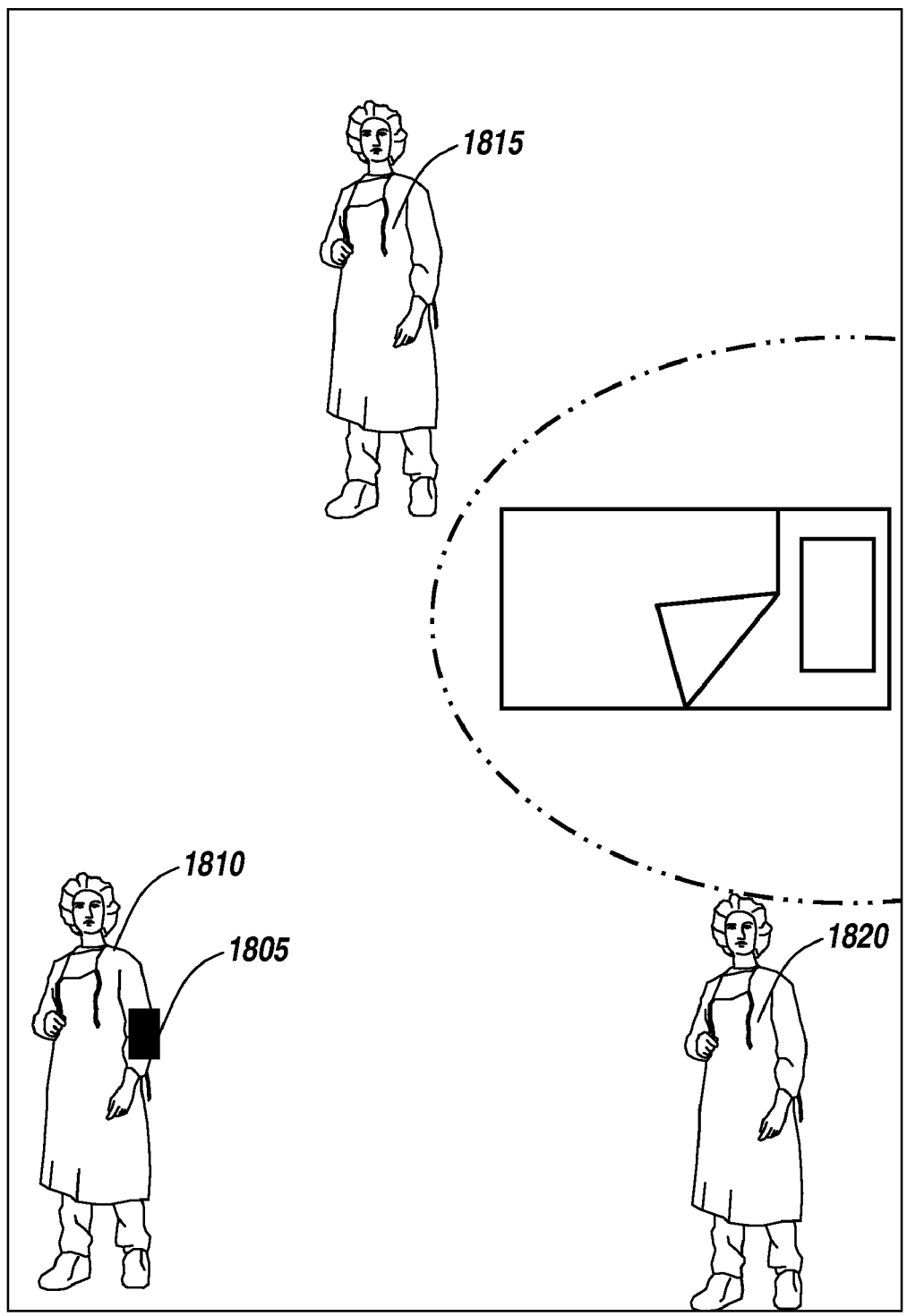
FIG. 18 depicts an exemplary embodiment of a system for enforcing a timeout protocol in an operating room.

FIG. 18 illustrates an exemplary system 1800 configured to enforce a timeout protocol in an operating room. Three hospital staff-members 1810, 1815 and 1820 will participate in a surgical procedure in the operating room, of whom staff-member 1810 is a designated staff-member charged with initiating and conducting the timeout protocol. The system 1800 includes a compliance zone designator 1805 attached to or otherwise associated with the designated staff-member 1810, which transmits an ultrasound signal to designate a compliance zone in the vicinity of the designated staff-member 1810. In this exemplary system, the compliance zone is a zone in or near which a protocol is conducted. The wearers of one or more wearable devices are expected to comply with the protocol in or near the compliance zone during the protocol. The system 1800 also includes multiple wearable devices, each worn by hospital staff-members 1810, 1815 and 1820 participating in the surgical procedure. The multiple wearable devices are configured to communicate with each other using ultrasound signals that may be encoded with information.

Upon deciding to initiate the timeout protocol, the designated staff-member activates the compliance zone designator 1805, e.g. by pushing an activation button. The compliance zone designator 1805 transmits an ultrasound signal thereby designating a compliance zone in the vicinity of the designated staff-member 1810. The ultrasound signal may be encoded with data which identifies the type of the compliance zone, e.g. that the zone is a timeout protocol zone in which a timeout protocol is performed. The data encoded in the ultrasound signal may also indicate the start of a window of time during which one or more wearers of wearable devices are expected to comply with the timeout protocol.

When the staff-members 1815-1820 are within the compliance zone, their wearable devices receive the ultrasound signal from the compliance zone designator 1805. In one exemplary embodiment, the wearable devices of the staff-members may be programmed to identify the interaction criteria of a timeout protocol associated with the compliance zone, based on the reception of the ultrasound signal. That is, upon receiving the ultrasound signal and optionally upon decoding the data in the signal, the wearable devices of the staff-members may determine that there is a timeout protocol that needs to be complied with in the operating room. In addition, the wearable devices may take one or more actions accordingly, e.g. flash a light or beep to indicate that a timeout protocol has started. In another exemplary embodiment, the wearable devices of the staff-members may not identify the interaction criteria of the timeout protocol and may not take actions accordingly.

During an exemplary timeout protocol, the designated staff-member 1810 announces the start of the protocol and reads aloud the patient's name and details of the surgical procedure. The other staff-members can record their agreement, disagreement or lack of awareness with the information read aloud using their individual wearable devices. For example, each of the other staff-members can press a button on his/her wearable device to transmit an ultrasound signal to indicate their agreement, or not transmit the ultrasound signal to indicate their disagreement or lack of awareness. The ultrasound signal may be encoded with information including, but not limited to, information identifying the wearable device or the staff-member transmitting the signal, information on the staff-member's agreement, disagreement or lack of awareness, etc. In an exemplary embodiment, the information may be encoded in a sequence of time intervals between consecutive bursts of the ultrasound signal transmitted by the staff-member's wearable device.

The wearable device of the designated staff-member 1810 receives the ultrasound transmissions from the staff-members. The wearable device of the designated staff-member 1810 is programmed to process and unpack the data encoded in the ultrasound signals, and record the reception of the ultrasound signals and the data encoded in the ultrasound signals. The responses from the staff-members may be recorded and processed individually or as a collection, and the processing may occur in real-time or after a post-response time period. In one exemplary embodiment, the wearable device of the designated staff-member 1810 receives ultrasound transmissions from the staff-members only during a predefined window of time after the start of the timeout protocol. In this embodiment, the wearable device stops recording or processing ultrasound transmissions from the staff-members after the predefined window of time expires.

According to an exemplary embodiment, the wearable device of the designated staff-member 1810 does not ensure that all staff-members have agreed to the information before the start of the surgical procedure. That is, the wearable device of the designated staff-member 1810 does not itself ensure compliance with the timeout protocol before the start of the procedure. In this embodiment, the wearable device records the reception of the ultrasound signals and the data encoded in the ultrasound signals. This record is later downloaded and further processed at a workstation at a base station to determine if all staff-members present at the procedure had agreed, who had agreed, who had disagreed, and who had failed to respond to the timeout protocol.

According to another exemplary embodiment, the wearable device of the designated staff-member 1810 ensures that all staff-members have agreed to the information before the start of the surgical procedure. That is, the wearable device of the designated staff-member 1810 itself takes part in ensuring compliance with the timeout protocol before the start of the procedure. In this embodiment, the wearable device determines the staff-members who are assigned to participate in the compliance zone. For example, the wearable device may use the information on the compliance zone, e.g. operating room identifier, to look up the staff-members who are assigned to participate in an operation in that operating room. Upon receiving an ultrasound signal from the other staff-members, the wearable device matches the data encoded in the signal to determine which staff-member originated the signal. Thus, the wearable device can record which of the staff-members responded in agreement, responded in disagreement, or did not respond at all. Upon determining that all staff-members responded in agreement, the wearable device may indicate a successful timeout, e.g. by beeping or by flashing a green light. In this case, the designated staff-member may then give the go ahead to the surgical procedure.

On the other hand, upon determining that not all staff-members responded or responded in agreement, the wearable device may indicate an unsuccessful timeout, e.g. by beeping or by flashing a red light. In this case, the designated staff-member may prevent the surgical procedure from starting until and unless the staff-members can come to a consensus.

Figure 19:
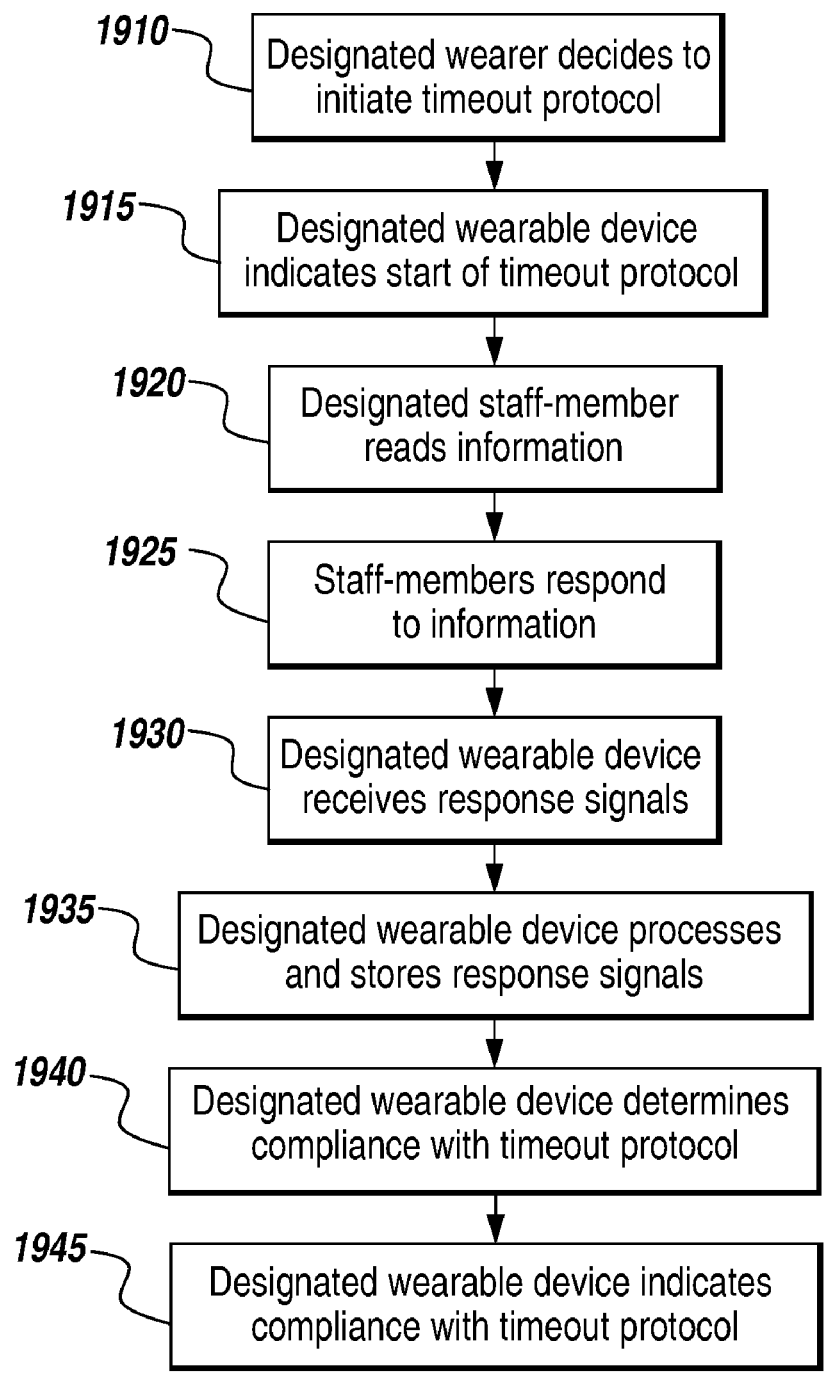
FIG. 19 is a flowchart of an exemplary method of monitoring and enforcing a timeout protocol in an operating room.

FIG. 19 depicts a flow chart 1900 of one exemplary embodiment of a method of the interaction between the wearable devices worn by participants in a surgical procedure during a timeout protocol. A designated staff-member who conducts the timeout protocol decides to initiate a timeout protocol (step 1910). The designated staff-member indicates the start of the timeout protocol (step 1915). In an exemplary embodiment, the designated staff-member can activate a compliance zone designator associated with the designated staff-member to transmit an ultrasound signal that designates a compliance zone in the vicinity. In another exemplary embodiment, the designated staff-member can transmit the ultrasound signal using an ultrasound transmitter built into the wearable device of the designated staff-member.

During the timeout protocol, the designated staff-member reads aloud information on the surgical procedure (step 1920). All the staff-members respond with their agreement, disagreement or lack of awareness to the information read aloud using their respective wearable devices, e.g. pressing a button on their wearable device to transmit an ultrasound signal (step 1925). The wearable device of the designated staff-member receives the response signals from the wearable devices of all the staff-members (step 1930), and processes and stores the response signals (step 1935).

Optionally, the wearable device of the designated staff-member determines compliance with the timeout protocol by determining if every staff-member has responded in agreement (step 1940). The wearable device then indicates whether every staff-member agreed to the timeout protocol, e.g. by flashing a green light, or whether any staff-member disagreed or failed to respond to the timeout protocol, e.g. by flashing a red light (step 1945).

VIII. Base Station

Another element of the system set forth in FIG. 13 is the base station 1350. In FIG. 13, the base station 1350 is located at the nurse's station 1355 in the corridor 1335. The base station 1350 is configured to communicate with wearable device 1345 for transferring data between the wearable device 1345 and the base station 1350. In this manner, compliance data can be downloaded from the wearable device 1345 and interaction criteria can be uploaded to configure the wearable device 1345. The base station 1350 may also be configured to communicate with one or more of the compliance zone designators 1305A and 1305B and hand washing stations 1325A and 1325B.

In the system set forth in FIG. 18, a base station may be provided to communicate with the wearable device associated with the designated staff-member 1810, for transferring data between the wearable device and the base station. In this manner, data on the timeout protocol can be downloaded from the wearable device, and interaction criteria on the timeout protocol can be uploaded to configure the wearable device. The base station may also be configured to communicate with the compliance zone designator 1805 and the wearable devices associated with the staff-members 1810, 1815 and 1820.

Figures 20, 21:
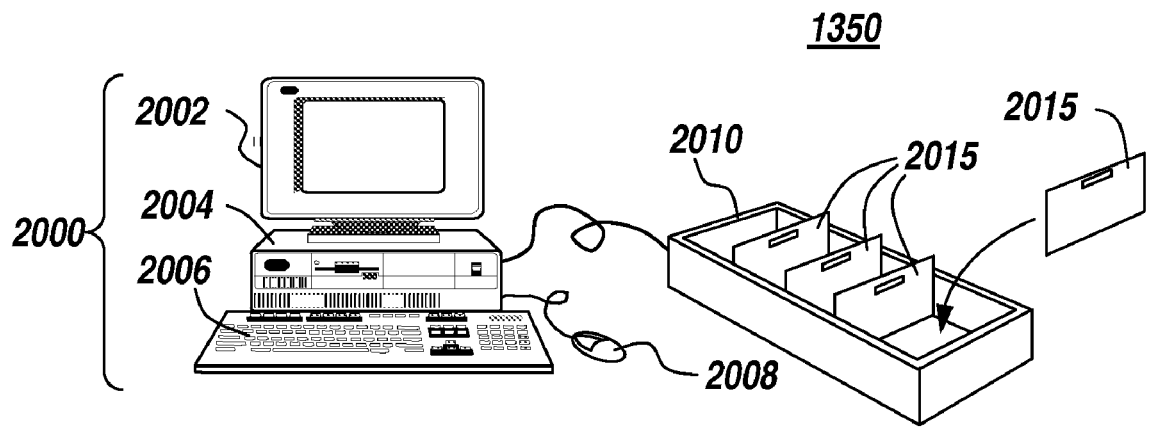
FIG. 20 depicts an exemplary embodiment of a base station.
FIG. 21 depicts an exemplary embodiment of a graphical user interface provided by a base station.

FIG. 20 depicts an exemplary embodiment of a base station 1350. In this embodiment, the base station 1350 includes a workstation 2000 and a wearable device rack 2010. The workstation 2000 may include a terminal 2002, a computer, such as a personal computer 2004, and input devices such as a keyboard 2006 and a mouse 2008. In other embodiments, the workstation may be a terminal 2002 connected to a remote or centrally located computer, such as a server. In other embodiments, the workstation 2000 may part of another system such as Electrical Medical Record (EMR) system.

The wearable device rack 2010 is connected the workstation 2000. For example, the wearable device rack 2010 may be connected via a USB connection. The wearable device rack 2010 provides a convenient place to deposit one or more wearable devices 2015 allowing data to be transferred to and from the wearable device 2015 to the workstation 2000. The wearable device rack 2010 may include a number of slots or cradles for receiving the wearable devices 2015. As mentioned previously, wearable devices such as the badge 500 or badge holder 600 may be provided with ports, such as USB ports, for transferring data and charging the batteries of the wearable device 2015. Each slot or cradle of the wearable device rack 2010 may be provided with a USB plug to mate with the respective USB port of the wearable device 2015. Placing the wearable device 2015 into a slot or cradle connects the wearable device 2015 to the workstation 2000 for charging and data transfer. For example, at the end of their shift, a hospital staff member may place there wearable device 2015 in the cradle allowing the wearable device to recharge, while the compliance data recorded for the shift is downloaded to the workstation 2000 for storage and analysis. Alternatively, the data transfer communication may take place using a wireless communication technology. In one exemplary embodiment, the wearable device 2015 is configured to store data collected over one or more weeks, so that the data stored on the wearable device 2015 need not be transferred to the workstation 2000 on a daily basis.

In accordance with some embodiments of the present invention, the base station 1350 does not include a wearable device rack 2010. Instead, the wearable device 2015 may communicate with the workstation 2000 of the base station 1350 directly using either a wired or wireless connection. In some such embodiments, the workstation 2000 may be located remotely or at a central location (such as a computer of data center) wherein the wearable device 2015 communicates wirelessly (using its internal transmitter and receiver or additional wireless technology) or via an Ethernet connection to the workstation 2000.

In exemplary embodiments, the base station 1350 may also be used to configure the wearable device 2015. For example, the interaction criteria that determine the hand washing requirements for the compliance zones 1315A and 1315B in FIG. 13 may be configured for the wearable device 1345 using the base station 730. An example of this can be seen in FIG. 21.

As previously discussed, in some embodiments, the base station 1350 of FIG. 13 may be configured to communicate wirelessly with one or more of the wearable device 1345, compliance zone designators 1305A and 1305B, and hand washing stations 1325A and 1325B. One advantage of such wireless communication is it allows for constant and continuous updates to the system. Thus, the compliance zones and interaction criteria can be updated or modified as needed. Likewise the status of wearable device 1345, compliance zone designators 1305A and 1305B and hand washing stations 1325A and 1325B may also continuously monitored.

As mentioned in the discussion of compliance zone designator 110, the receiver 220 of the compliance zone designator 110 may be used to receive signals for configuring the compliance zone designator 110. As mentioned in the discussion of the wearable device 120, the receiver 400 of the wearable device 120 may be used to receive signals for configuring the wearable device 120. Likewise, the one or more transmitters 440 of the wearable device 120 may be used to transfer recorded compliance data. Similarly, the transmitters 1330A and 1330B and as receiver (not shown) of the hand washing stations 1325A and 1325B may also be used to transfer data to and from the base station 1350.

Once data is obtained from the wearable device 1345, compliance zone designators 1305A and 1305B, and hand washing stations 1325A and 1325B, the data can be stored and analyzed. This data can be used to determine how well the protocols and requirements are being enforced. In the hand washing example, hospital administrators can use the data to determine if hand washing protocol goals are being met, determine who is or is not complying with the hand washing protocols, and further configure the system to improve compliance. In some embodiments, incentives or demerits may be provided based on an individual's compliance. The data can also be used in providing robust comprehensive documentation on group compliance for submission to regulatory or accrediting bodies.

FIG. 21 depicts an example graphical user interface (GUI) 2100 used to register the wearable device to associate a badge with a particular hospital staff member. In this embodiment, the GUI provides a number of fields to be filled in by a user. The first field is the badge number field 2105. In the badge number field 2105, the user enters the identification number of the wearable device being configured. The next field is the badge wearer field 2110. In the badge wearer field 2110, the user enters the name of the hospital staff member with whom the wearable device is to be associated. The next field is the role field 2115. In role field 2115, the user identifies the role of the hospital staff member associated with the wearable device. For example, the role of the hospital staff member may be "doctor," "nurse," or the like. The final displayed field is the certification field 2120. In certification field 2120, the user enters the certification level of the hospital staff member associated with the wearable device. For example, the hospital staff member may be certified in infectious medicine. Based on the information provided by the user, the wearable device may then be configured for the particular hospital staff member. For example, if the hospital staff member is a doctor certified in infectious medicine, the wearable device may be configured to allow the doctor to activate the override on the wearable device when in a compliance zone. Likewise, the time limit for washing the doctor's hands after entering or leaving the compliance zone may also be adjusted.

It should be understood that the fields 2105, 2110, 2115 and 2120 depicted in FIG. 21 are but a few of a number of possible fields. In accordance with some example embodiments of the present invention, other fields may be provided depending on the information entered in previous fields. In other embodiments, the field may be provided to specify individually each interaction criteria. In certain embodiments, the fields provided may depend on the identity of the user of the base station. That is, the ability to configure a wearable device may require authorization and/or authentication. For example, a department head may be provided with more ability to configure a badge than an individual doctor or nurse in the department.

Thus, the system and methodologies of the present invention provide an effective means to enforce protocols necessary to comply with health, safety, insurance, and regulatory requirements. A compliance zone designator is placed at the location enforcement of the protocols is desired. The compliance zone designators transmit a signal that determines a compliance zone. Employees are provided with wearable devices that can receive the signal transmitted by the compliance zone identifier. When a wearable device is within the compliance zone, the wearable device recognizes the compliance zone and identifies the interaction criteria for the compliance zone. The interaction criteria are requirements necessary to comply with the desired protocols. The wearable device determines and records compliance with the interaction criteria. The recorded compliance data may then be analyzed to determine the level of compliance with the protocols being enforced.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. It is intended that the present invention be limited only to the extent required by the appended claims and the applicable rules of law.

It is also to be understood that the following claims are to cover all generic and specific features of the invention described herein, and all statements of the scope of the invention that, as a matter of language, might be said to fall therebetween.

We claim:

1. A system for establishing a compliance zone and interacting therewith, the system comprising:
    a compliance zone designator configured to transmit data using an ultrasound signal in such a way that results in creation of the compliance zone in a vicinity of the compliance zone designator, the ultrasound signal comprising a plurality of bursts, wherein consecutive bursts within the plurality of bursts are separated in time by predefined time intervals, and wherein a sequence of all the predefined time intervals between the consecutive bursts within the plurality of bursts uniquely identifies the compliance zone; and
    a wearable device separate from the compliance zone designator, the wearable device comprising a compliance zone recognition component configured to identify a pre-defined interaction criterion for the compliance zone when the wearable device receives the data through the ultrasound signal within the compliance zone;
    wherein upon the wearable device being disposed within the compliance zone, the compliance zone recognition component identifies the interaction criterion of the compliance zone and operates in accordance with the interaction criterion.

2. The system of claim 1, wherein the compliance zone designator is mobile.

3. The system of claim 1, wherein the compliance zone designator transmits 7 bursts of the ultrasound signal, and 8-10 carrier cycles per burst, each burst being a sequence of 6 pulses in which all time intervals between consecutive pulses are within a valid range.

4. The system of claim 3, wherein the valid range is between 23 and 27 microseconds, inclusive.

5. The system of claim 3, wherein the data on the compliance zone is encoded in all the predefined time intervals between consecutive bursts within the 7 bursts of the ultrasound signal.

6. The system of claim 3, wherein:
    each time interval between two consecutive bursts corresponds to an alphanumeric character of data; and
    a collection of all characters of the data encoded in the 7 bursts corresponds to the data on the compliance zone.

7. The system of claim 3, wherein, for each burst of the ultrasound signal the compliance zone recognition component is further configured to:
    recognize a single burst of ultrasound signal after receiving the 6 pulses in which all the time intervals between consecutive pulses are within the valid range; and
    minimize multipath interference of the ultrasound signal received at the compliance zone recognition component by ignoring additional pulses received after recognizing the single burst for a blackout period.

8. The system of claim 7, wherein the blackout period is at least 30 milliseconds.

9. The system of claim 1, wherein the wearable device further comprises:
    a processor which processes a received ultrasound signal to decode the data encoded in the ultrasound signal; and
    a controller which controls the processor of the wearable device.

10. The system of claim 9, wherein a clock of the controller is a low-power RC timer oscillator.

11. The system of claim 9, wherein the wearable device further comprises:
    a filter that filters out components of a received signal that do not correspond to an ultrasound signal, wherein the controller and processor are activated only when an ultrasound signal passes through and is output by the filter.

12. The system of claim 1, wherein the data on the compliance zone comprises:
    a zone identifier for the compliance zone; and
    a CRC checksum that is used to determine if the zone identifier is valid.

13. A method of establishing a compliance zone and interacting therewith, the method comprising:
    transmitting data using an ultrasound signal using a compliance zone designator in such a way that results in creation of the compliance zone in a vicinity of the compliance zone designator, the ultrasound signal comprising a plurality of bursts, wherein consecutive bursts within the plurality of burst are separated in time by predefined time intervals, and wherein a sequence of all the predefined time intervals between the consecutive bursts within the plurality of bursts uniquely identifies the compliance zone; and
    identifying a pre-defined interaction criterion for the compliance zone using a compliance zone recognition component of a wearable device when the wearable device receives the data through the ultrasound signal within the compliance zone, wherein the compliance zone recognition component operates in accordance with the interaction criterion.

14. The method of claim 13, wherein the compliance zone designator is mobile.

15. The method of claim 13, further comprising:
    transmitting 7 bursts of the ultrasound signal using the compliance zone designator, and 8-10 carrier cycles per burst, each burst being a sequence of 6 pulses in which all time intervals between consecutive pulses are within a valid range.

16. The method of claim 15, wherein the valid range is between 23 and 27 microseconds, inclusive.

17. The method of claim 15, wherein the data on the compliance zone is encoded in all the predefined time intervals between consecutive bursts within the 7 bursts of the ultrasound signal.

18. The method of claim 17, wherein:
each time interval between two consecutive bursts corresponds to an alphanumeric character of data; and
a collection of all characters of the data encoded in the 7 bursts corresponds to the data on the compliance zone.

19. The method of claim 15, further comprising, for each burst of the ultrasound signal:
recognizing a single burst of ultrasound signal using the compliance zone recognition component after receiving the 6 pulses in which all the time intervals between consecutive pulses are within the valid range; and
minimizing multipath interference in the ultrasound signal received at the compliance zone recognition component by ignoring additional pulses received at the compliance zone recognition component after recognizing the single burst for a blackout period.

20. The method of claim 19, wherein the blackout period is at least 30 milliseconds.

21. The method of claim 13, further comprising:
processing a received ultrasound signal using a processor to decode the data encoded in the ultrasound signal; and
controlling the processor using a controller.

22. The method of claim 21, further comprising:
tracking time in the controller using a low-power RC timer oscillator.

23. The method of claim 21, further comprising:
filtering out components of a received signal that do not correspond to an ultrasound signal using a filter; and
activating the controller and the processor only when an ultrasound signal passes through and is output by the filter.

24. The method of claim 13, wherein the data on the compliance zone comprises:
a zone identifier for the compliance zone; and
a CRC checksum that is used to determine if the zone identifier is valid.

25. A method comprising:
transmitting a first ultrasound signal in such a way that results in creation of a compliance zone in a vicinity of the transmission of the first ultrasound signal;
receiving the first ultrasound signal at a first wearable device;
identifying an interaction criterion associated with the compliance zone using the first wearable device when the first wearable device receives the first ultrasound signal within the compliance zone;
performing an action associated with the interaction criterion using the first wearable device, the action including transmitting a second ultrasound signal communicating with a second wearable device;
receiving the second ultrasound signal from the first wearable device at the second wearable device; and
recording receipt of the second ultrasound signal at the second wearable device.

26. A system for establishing a compliance zone, the system comprising:
a controller programmed to control a transmitter to transmit a plurality of bursts of an ultrasound signal, wherein consecutive bursts within the plurality of bursts are separated in time by predefined time intervals, and wherein a sequence of all the predefined time intervals between the consecutive bursts within the plurality of bursts uniquely identifies the compliance zone;
wherein the transmitter is configured to transmit the plurality of bursts of the ultrasound signal in such a way that results in creation of the compliance zone in a vicinity of the system.

27. The system of claim 26, wherein the transmitter transmits 7 bursts of the ultrasound signal, and 8-10 carrier cycles per burst, each burst being a sequence of 6 pulses in which all time intervals between consecutive pulses are within a valid range.

28. The system of claim 27, wherein the valid range is between 23 and 27 microseconds, inclusive.

29. The system of claim 27, wherein:
each time interval between two consecutive bursts corresponds to an alphanumeric character of data; and
a collection of all characters of the data encoded in the 7 bursts corresponds to the data on the compliance zone.

30. A system for recognizing a compliance zone, the system comprising:
a receiver configured to receive an ultrasound signal establishing the compliance zone; and
a processor programmed to:
recognize a plurality of bursts of the ultrasound signal, wherein consecutive bursts within the plurality of bursts are separated in time by predefined time intervals;
decode a sequence of all the predefined time intervals between the consecutive bursts within the plurality of bursts, the sequence uniquely identifying the compliance zone; and
identify a pre-defined interaction criterion for the compliance zone based on the identity of the compliance zone.

31. The system of claim 30, wherein, for each burst of the ultrasound signal, the processor is programmed to:
recognize a single burst of ultrasound signal after receiving a first number of pulses in which all the time intervals between consecutive pulses are within a valid range; and
minimize multipath interference of the ultrasound signal received at the receiver by ignoring additional pulses received after recognizing the single burst for a blackout period.

32. The system of claim 31, wherein the first number of pulses is 6.

33. The system of claim 31, wherein the valid range is between 23 and 27 microseconds, inclusive.

34. The system of claim 31, wherein the blackout period is at least 30 milliseconds.

* * * * *